United States Patent [19]

Sum et al.

[11] Patent Number: 5,495,030

[45] Date of Patent: Feb. 27, 1996

[54] 9-[(SUBSTITUTED GLYCYL)AMIDO)]-6-DEMETHYL-6-DEOXY-TETRACYCLINES

[75] Inventors: Phaik-Eng Sum, Pomona; Ving J. Lee, Monsey, both of N.Y.; Raymond T. Testa, Cedar Grove, N.J.

[73] Assignee: American Cyanamid Company, Wayne, N.J.

[21] Appl. No.: 299,769

[22] Filed: Sep. 1, 1994

Related U.S. Application Data

[62] Division of Ser. No. 928,590, Aug. 13, 1992, Pat. No. 5,442,059.

[51] Int. Cl.$^6$ .................................................. C07C 50/22
[52] U.S. Cl. ............................................................. 552/205
[58] Field of Search ............................................. 552/205

[56]   References Cited

U.S. PATENT DOCUMENTS

| | | | |
|---|---|---|---|
| Re. 26,253 | 8/1967 | Petisi | 552/205 |
| Re. 26,271 | 9/1967 | Boothe | 552/205 |
| 3,145,228 | 8/1964 | Schach von Wittenau | 552/205 |
| 3,148,212 | 9/1964 | Boothe | 552/205 |
| 3,200,149 | 8/1965 | Blackwood | 552/205 |
| 3,239,499 | 3/1966 | Rennhard | 552/205 |
| 3,250,809 | 5/1966 | Blackwood | 552/205 |
| 3,250,810 | 5/1966 | Blackwood | 552/205 |
| 3,338,963 | 8/1967 | Petisi | 552/205 |
| 3,341,585 | 9/1967 | Bitha | 552/205 |
| 3,345,410 | 10/1967 | Winterbottom | 552/205 |
| 3,360,561 | 12/1967 | Lambiano | 552/205 |
| 3,373,196 | 3/1968 | Bitha | 552/205 |
| 3,373,197 | 3/1968 | Martell | 552/205 |
| 3,373,198 | 3/1968 | Martell | 552/205 |
| 3,397,230 | 8/1968 | Winterbottom | 552/205 |
| 3,433,834 | 3/1969 | Winterbottom | 552/205 |
| 3,502,696 | 3/1970 | Conover | 552/205 |
| 3,509,184 | 4/1970 | Conover | 552/205 |
| 3,515,731 | 6/1970 | Conover | 552/205 |
| 3,518,306 | 6/1970 | Martell | 552/205 |
| 3,697,552 | 10/1972 | Conover | 552/205 |
| 3,772,363 | 11/1973 | Conover | 552/205 |
| 3,829,453 | 8/1974 | Conover | 552/205 |
| 3,849,493 | 11/1974 | Conover | 552/205 |
| 5,281,628 | 1/1994 | Hlauka et al. | 552/205 |
| 5,284,963 | 2/1994 | Sum et al. | 552/205 |
| 5,371,076 | 12/1994 | Lee et al. | 552/205 |
| 5,380,888 | 1/1995 | Sum et al. | 552/205 |
| 5,386,041 | 1/1995 | Sum et al. | 552/205 |
| 5,420,272 | 5/1995 | Sum et al. | 552/205 |
| 5,430,162 | 7/1995 | Sum | 552/205 |
| 5,442,059 | 8/1995 | Sum et al. | 552/205 |

*Primary Examiner*—Kimberly J. Kestler
*Attorney, Agent, or Firm*—T. S. Szatkowski

[57]   ABSTRACT

The invention provides compounds of the formula:

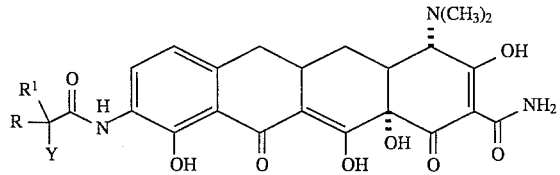

wherein R, $R^1$ and Y are defined in the specification. The compounds are useful for the production of 6-demethyl-6-deoxytracycline derivatives.

25 Claims, No Drawings

9-[(SUBSTITUTED GLYCYL)AMIDO]-6-DEMETHYL-6-DEOXYTETRACYCLINES

This is a divisional of application Ser. No. 07/928,590 filed on Aug. 13, 1992 now U.S. Pat. No. 5,442,059.

BACKGROUND OF THE INVENTION

1. Field of the Invention

The invention relates to novel [4S-(4alpha, 12aalpha)]-4-(dimethylamino)-9-[[(substituted amino)substituted] amino]-1,4,4a,5,5a,6,11,12a-octahydro- 3,10,12,12a-tetrahydroxy-1,11-dioxo-2-naphthacenecarboxamides herein after called 9-[(substituted glycyl)amido] -6-demethyl-6-deoxytetracyclines, which exhibit antibiotic activity against a wide spectrum of organisms including organisms which are resistant to tetracyclines and are useful as antibiotic agents.

The invention also relates to novel 9-[(haloacyl)amido]-6-demethyl-6-deoxytetracycline intermediates useful for making the novel compounds of the present invention and to novel methods for producing the novel compounds and intermediate compounds.

SUMMARY OF THE INVENTION

This invention is concerned with novel 9-[(substituted glycyl)amido]-6-demethyl-6-deoxytetracyclines represented by formula I and II, which have antibacterial activity; with methods of treating infectious diseases in warm blooded animals employing these new compounds; with pharmaceutical preparations containing these compounds; with novel intermediate compounds and processes for the production of these compounds. More particularly, this invention is concerned with compounds of formula I and II which have enhanced in vitro and in vivo antibacterial activity against tetracycline resistant strains as well as a high level of activity against strains which are normally susceptible to tetracyclines.

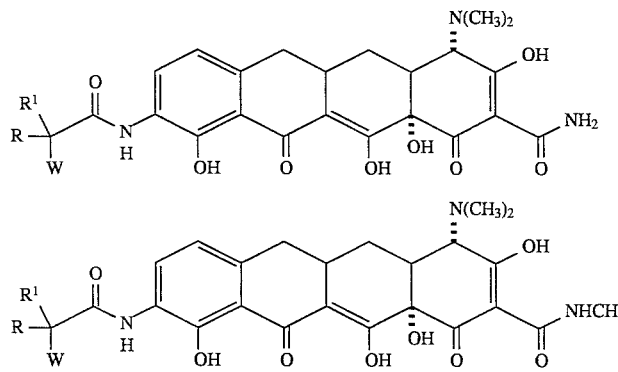

In formula I and II, R is selected from hydrogen; straight or branched ($C_1$–$C_8$)alkyl group selected from methyl, ethyl, propyl, isopropyl, butyl, isobutyl, pentyl, hexyl, heptyl and octyl; α-mercapto($C_1$–$C_4$)alkyl group selected from mercaptomethyl, α-mercaptoethyl, α-mercapto-1-methylethyl, α-mercaptopropyl and α-mercaptobutyl; α-hydroxy($C_1$–$C_4$)alkyl group selected from hydroxymethyl, α-hydroxyethyl, α-hydroxy-1-methylethyl, α-hydroxypropyl and α-hydroxybutyl; carboxyl($C_1$–$C_8$)alkyl group; ($C_6$–$C_{10}$)aryl group selected from phenyl, α-naphthyl and β-naphthyl; substituted($C_6$–$C_{10}$)aryl group (substitution selected from hydroxy, halogen, ($C_1$–$C_4$)alkoxy, trihalo($C_1$–$C_3$) alkyl, nitro, amino, cyano, ($C_1$–$C_4$)alkoxycarbonyl, ($C_1$–$C_3$)alkylamino and carboxy); ($C_7$–$C_9$)aralkyl group selected from benzyl, 1-phenylethyl, 2-phenylethyl and phenylpropyl; substituted($C_7$–$C_9$)aralkyl group [substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy];

$R^1$ is selected from hydrogen and ($C_1$–$C_6$)alkyl selected from methyl, ethyl propyl, isopropyl, butyl, isobutyl, pentyl and hexyl;

when R does not equal $R^1$ the stereochemistry of the asymmetric carbon (i.e. the carbon bearing the W substituent) maybe be either the racemate (DL) or the individual enantiomers (L or D);

W is selected from amino; hydroxylamino; ($C_1$–$C_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; ($C_3$–$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, and bicyclo[2.2.2]oct-2-yl and the diastereomers and enantiomers of said ($C_3$–$C_8$)cycloalkyl monosubstituted amino group; [($C_4$–$C_{10}$)cycloalkyl]alkyl monosubstituted amino group substitution selected from (cyclopropyl)methyl, (cyclopropyl)ethyl, (cyclobutyl)methyl, (trans- 2-methylcyclopropyl)methyl, and (cis-2-methylcyclobutyl)methyl; ($C_3$–$C_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl 2-cyclopentenyl and 2-cyclohexenyl; ($C_6$–$C_{10}$)aryl monosubstituted amino group substitution selected from phenyl and naphthyl; ($C_7$–$C_{10}$)aralkylamino group substitution selected from benzyl, 2-phenylethyl, 1-phenylethyl, 2-(naphthyl)methyl, 1-(naphthyl)methyl and phenylpropyl; substituted ($C_6$–$C_{10}$)aryl monosubstituted amino group [substitution selected from ($C_1$–$C_5$)acyl, ($C_1$–$C_5$)acylamino, ($C_1$–$C_4$)alkyl, mono or disubstituted ($C_1$–$C_8$)alkylamino, ($C_1$–$C_4$)alkoxy, ($C_1$–$C_4$)alkoxycarbonyl, ($C_1$–$C_4$)alkylsulfonyl, amino, carboxy, cyano, halogen, hydroxy, nitro and trihalo($C_1$–$C_3$)alkyl]; straight or branched symmetrical disubstituted ($C_2$–$C_{14}$)alkylamino group substitution selected from dimethyl, diethyl, diisopropyl, di-n-propyl, di-n-butyl and diisobutyl; symmetrical disubstituted (C$_3$–C$_{14}$)cycloalkylamino group substitution selected from dicyclopropyl, dicyclobutyl, dicyclopentyl, dicyclohexyl and dicycloheptyl; straight or branched unsymmetrical disubstituted (C$_3$–C$_{14}$)alkylamino group wherein the total number of carbons in the substitution is not more than 14; unsymmetrical disubstituted (C$_4$–C$_{14}$)cycloalkylamino group wherein the total number of carbons in the substitution is not more than 14; (C$_2$–C$_8$)azacycloalkyl and substituted (C$_2$–C$_8$)azacycloalkyl group substitution selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, and 2-azabicyclo[2.2.2]oct-2-yl and the diastereomers and enantiomers of said (C$_2$–C$_8$)azacycloalkyl and substituted (C$_2$–C$_8$)azacycloalkyl group; 1-azaoxacycloalkyl group selected from morpholinyl and 1-aza-5-oxocycloheptane; substituted 1-azaoxacycloalkyl group substitution selected from 2-(C$_1$–C$_3$)alkylmorpholinyl, 3-(C$_1$–C$_3$)alkylisooxazolidinyl, tetrahydrooxazinyl and 3,4-dihydrooxazinyl; [1,n]-diazacycloalkyl and substituted [1,n]-diazacycloalkyl group selected from piperazinyl, 2-(C$_1$–C$_3$)alkylpiperazinyl, 4-(C$_1$–C$_3$)alkylpiperazinyl, 2,4-dimethylpiperazinyl, 4-(C$_1$–C$_4$)alkoxypiperazinyl, 4-(C$_6$–C$_{10}$)aryloxypiperazinyl, 4-hydroxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, and 2,5-diaza-5,7-dimethylbicyclo[2.2.2]oct-2-yl and the diastereomers or enantiomers of said 1,n]-diazacycloalkyl and substituted 1,n]-diazacycloalkyl group; 1-azathiacycloalkyl and substituted 1-azathiacycloalkyl group selected from thiomorpholinyl, 2-(C$_1$–C$_3$)alkylthiomorpholinyl and 3-(C$_3$–C$_6$)cycloalkylthiomorpholinyl; N-azolyl and substituted N-azolyl group selected from 1-imidazolyl, 2-(C$_1$–C$_3$)alkyl-1-imidazolyl, 3-(C$_1$–C$_3$)alkyl-1-imidazolyl, 1-pyrrolyl, 2-(C$_1$–C$_3$)alkyl-1-pyrrolyl, 3-(C$_1$–C$_3$)alkyl-1-pyrrolyl, 1-pyrazolyl, 3-(C$_1$–C$_3$)alkyl- 1-pyrazolyl, indolyl, 1-(1,2,3-triazolyl), 4-(C$_1$–C$_3$)alkyl-1-(1,2,3-triazolyl), 5-(C$_1$–C$_3$)alkyl-1-( 1,2,3-triazolyl), 4-(1,2,4-triazolyl, 1-tetrazolyl, 2-tetrazolyl and benzimidazolyl; (heterocycle)amino group said heterocycle selected from 2- or 3-furanyl, 2- or 3-thienyl, 2-, 3- or 4-pyridyl, 2- or 5-pyridazinyl, 2-pyrazinyl, 2-(imidazolyl), (benzimidazolyl), and (benzothiazolyl) and substituted (heterocycle)amino group (substitution selected from straight or branched (C$_1$–C$_6$)alkyl); (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group (substitution selected from straight or branched (C$_1$–C$_6$)alkyl); carboxy(C$_2$–C$_4$)alkylamino group selected from aminoacetic acid, α-aminopropionic acid, β-aminopropionic acid, α-butyric acid, and β-aminobutyric acid and the enantiomers of said carboxy(C$_2$–C$_4$)alkylamino group; (C$_1$–C$_4$)alkoxycarbonylamino group substitution selected from methoxycarbonyl, ethoxycarbonyl, allyloxycarbonyl, propoxycarbonyl, isoproproxycarbonyl, 1,1-dimethylethoxycarbonyl, n-butoxycarbonyl, and 2-methylpropoxycarbonyl; (C$_1$–C$_4$)alkoxyamino group substitution selected from methoxy, ethoxy,n-propoxy, 1-methylethoxy, n-butoxy, 2-methylpropoxy, and 1,1-dimethylethoxy; (C$_3$–C$_8$)cycloalkoxyamino group selected from cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, and bicyclo[2.2.2]oct-2-yloxy and the diastereomers and enantiomers of said (C$_3$–C$_8$)cycloalkoxyamino group; (C$_6$–C$_{10}$)aryloxyamino group selected from phenoxyamino, 1-naphthyloxyamino and 2-naphthyloxyamino; (C$_7$–C$_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

R$^2$ is selected from hydrogen; straight or branched (C$_1$–C$_3$)alkyl group selected from methyl, ethyl, n-propyl or 1-methylethyl; (C$_6$–C$_{10}$)aryl group selected from phenyl, α-naphthyl or β-naphthyl; (C$_7$–C$_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

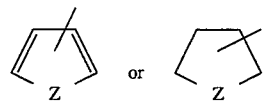

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

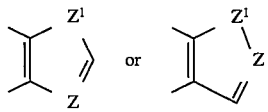

Z or Z$^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

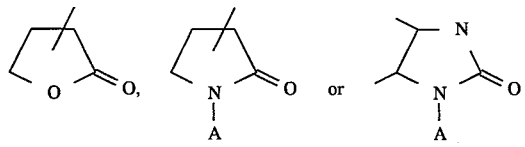

(A is selected from hydrogen; straight or branched (C$_1$–C$_4$)alkyl; C$_6$-aryl; substituted C$_6$-aryl (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C$_1$–C$_3$) alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —(CH$_2$)$_n$COOR$^4$ where n=0–4 and R$^4$ is selected from hydrogen; straight or branched (C$_1$–C$_3$)alkyl group selected from methyl, ethyl, n-propyl or 1-methylethyl; or (C$_6$–C$_{10}$)aryl group selected from phenyl, α-naphthyl, or β-naphthyl; R$^3$ is selected from hydrogen; straight or branched (C$_1$–C$_3$)alkyl group selected from methyl, ethyl, n-propyl or 1-methylethyl; (C$_6$–C$_{10}$)aryl group selected from phenyl, α-naphthyl or β-naphthyl; (C$_7$–C$_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

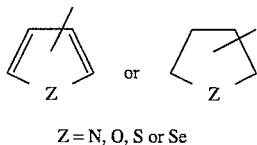

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

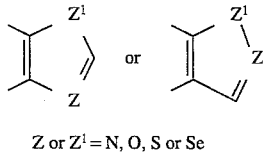

Z or Z$^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

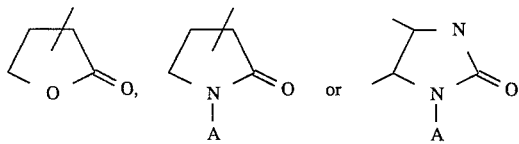

(A is selected from hydrogen; straight or branched (C$_1$–C$_4$)alkyl; C$_6$-aryl; substituted C$_6$-aryl (substitution selected from halo, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino or carboxy); (C$_7$–C$_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or (C$_1$–C$_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —(CH$_2$)$_n$COOR$^4$ where n=0–4 and R$^4$ is selected from hydrogen; straight or branched (C$_1$–C$_3$)alkyl selected from methyl, ethyl, n-propyl or 1-methylethyl; or (C$_6$–C$_{10}$)aryl selected from phenyl, α-naphthyl or β-naphthyl; with the proviso that R$^2$ and R$^3$ cannot both be hydrogen;

or R$^2$ and R$^3$ taken together are —(CH$_2$)$_2$B(CH$_2$)$_2$—, wherein B is selected from (CH$_2$)$_n$ and n=0–1, —NH, —N(C$_1$–C$_3$)alkyl [straight or branched], —N(C$_1$–C$_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Preferred compounds are compounds according to the above formula I and II wherein: R is selected from hydrogen; straight or branched (C$_1$–C$_8$)alkyl group selected from methyl, ethyl, propyl, isopropyl, butyl, isobutyl, pentyl, hexyl, heptyl and octyl; α-mercapto(C$_1$–C$_4$)alkyl group selected from mercaptomethyl, α-mercaptoethyl, α-mercapto-1-methylethyl, α-mercaptopropyl and α-mercaptobutyl; α-hydroxy(C$_1$–C$_4$)alkyl group selected from hydroxymethyl, α-hydroxyethyl, α-hydroxy-1-methylethyl, α-hydroxypropyl and α-hydroxybutyl; carboxyl(C$_1$–C$_8$)alkyl group; (C$_6$–C$_{10}$)aryl group selected from phenyl, α-naphthyl and β-naphthyl; (C$_7$–C$_9$)aralkyl group selected from benzyl, 1-phenylethyl, 2-phenylethyl and phenylpropyl; substituted(C$_7$–C$_9$)aralkyl group [substitution selected from halo, (C$_1$–C$_4$)alkyl, nitro, hydroxy, amino, mono- or di-substituted (C$_1$–C$_4$)alkylamino, (C$_1$–C$_4$)alkoxy, (C$_1$–C$_4$)alkylsulfonyl, cyano and carboxy];

R$^1$ is selected from hydrogen and (C$_1$–C$_6$)alkyl selected from methyl, ethyl propyl, isopropyl, butyl, isobutyl, pentyl and hexyl;

when R does not equal R$^1$ the stereochemistry of the asymmetric carbon (i.e. the carbon bearing the W substituent) maybe be either the racemate (DL) or the individual enantiomers (L or D);

W is selected from amino; hydroxylamino; (C$_1$–C$_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; (C$_3$–C$_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, and bicyclo[2.2.2]oct-2-yl and the diastereomers and enantiomers of said (C$_3$–C$_8$)cycloalkyl monosubstituted amino group; [(C$_4$–C$_{10}$)cycloalkyl]alkyl monosubstituted amino group substitution selected from(cyclopropyl)methyl, (cyclopropyl)ethyl, (cyclobutyl)methyl, (trans-2-methylcyclopropyl)methyl, and (cis-2-methylcyclobutyl)methyl; (C$_3$–C$_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl 2-cyclopentenyl and 2-cyclohexenyl; (C$_6$–C$_{10}$)aryl monosubstituted amino group substitution selected from phenyl and naphthyl; (C$_7$–C$_{11}$)aralkylamino group substitution selected from benzyl, 2-phenylethyl, 1-phenylethyl, 2-(naphthyl)methyl, 1-(naphthyl)methyl and phenylpropyl; straight or branched symmetrical disubstituted (C$_2$–C$_{14}$)alkylamino group substitution selected from dimethyl, diethyl, diisopropyl and di-n-propyl; symmetrical disubstituted (C$_3$–C$_{14}$)cycloalkylamino group substitution selected from dicyclopropyl, dicyclobutyl, dicyclopentyl, dicylohexyl and dicycloheptyl; straight or branched unsymmetrical disubstituted ($C_3$–$C_{14}$)alkylamino group wherein the total number of carbons in the substitution is not more than 14; unsymmetrical disubstituted ($C_4$–$C_{14}$)cycloalkylamino group wherein the total number of carbons in the substitution is not more than 14; ($C_2$–$C_8$)azacycloalkyl and substituted ($C_2$–$C_8$)azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, and 2-azabicyclo[2.2.2]oct-2-yl and the diastereomers and enantiomers of said ($C_2$–$C_8$)azacycloalkyl and substituted ($C_2$–$C_8$)azacycloalkyl group; 1-azaoxacycloalkyl group selected from morpholinyl and 1-aza-5-oxacycloheptane; substituted 1-azaoxacycloalkyl group selected from 2-($C_1$–$C_3$)alkylmorpholinyl, 3-($C_1$–$C_3$)alkylisoxazolidinyl, tetrahydrooxazinyl and 3,4-dihydrooxazinyl; [1,n]-diazacycloalkyl and substituted [1,n]-diazacycloalkyl group selected from piperazinyl, 2-($C_1$–$C_4$)alkylpiperazinyl, 4-($C_1$–$C_3$)alkylpiperazinyl, 2,4-dimethylpiperazinyl, 4-($C_1$–$C_3$)alkoxypiperazinyl, 4-($C_6$–$C_{10}$)aryloxypiperazinyl, 4-hydroxypiperazinyl, 2,5-diazabicyclo-[ 2.2.1]hept-2-yl, 2,5-diaza-5-methylbicyclo-[ 2.2.1]hept-2-yl, 2,3-diaza-3-methylbicyclo[2.2.2]-oct- 2-yl, and 2,5-diaza-5,7-dimethylbicyclo[2.2.2]oct- 2-yl and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl- 1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl- 1-pyrrolyl, 1-pyrazolyl, 3-($C_1$–$C_3$)alkyl-1- pyrazolyl, indolyl, 1-(1,2,3-triazo- lyl), 4-alkyl-1-(1,2,3-triazolyl), 5-($C_1$–$C_3$)alkyl-1- (1,2,3-triazolyl), 4-(1,2,4-triazolyl, 1-tetrazolyl, 2-tetrazolyl and benzimidazolyl; (heterocycle)amino group said heterocycle selected from 2- or 3-furanyl, 2- or 3-thienyl, 2-, 3- or 4-pyridyl, 2- or 5-pyridazinyl, 2-pyrazinyl, 2-(imidazolyl), (benzimidazolyl), and (benzothiazolyl) and substituted (heterocycle)amino group (substitution selected from straight or branched ($C_1$–$C_6$)alkyl); (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group (substitution selected from straight or branched ($C_1$–$C_6$)alkyl); carboxy($C_2$–$C_4$)alkylamino group selected from aminoacetic acid, α-aminopropionic acid, β-aminopropionic acid, α-butyric acid, and β-aminobutyric acid and the enantiomers of said carboxy($C_2$–$C_4$)alkylamino group; ($C_1$–$C_4$)alkoxycarbonylamino group substitution selected from methoxycarbonyl, ethoxycarbonyl, allyloxycarbonyl, propoxycarbonyl, isoproproxycarbonyl, 1,1-dimethylethoxycarbonyl, n-butoxycarbonyl, and 2-methylpropoxycarbonyl; ($C_1$–$C_4$)alkoxyamino group substitution selected from methoxy, ethoxy,n-propoxy, 1-methylethoxy, n-butoxy, 2-methylpropoxy, and 1,1-dimethylethoxy; ($C_3$–$C_8$)cycloalkoxyamino group substitution selected from cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, and bicyclo[2.2.2]oct-2-yloxy and the diastereomers and enantiomers of said ($C_3$–$C_8$)cycloalkoxyamino group; ($C_6$–$C_{10}$)aryloxyamino group selected from phenoxyamino, 1-naphthyloxyamino and 2-naphthyloxyamino; ($C_7$–$C_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

$R^2$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

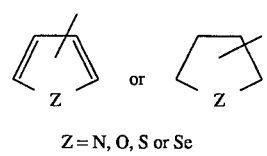

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

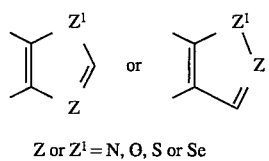

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended heteroatom:

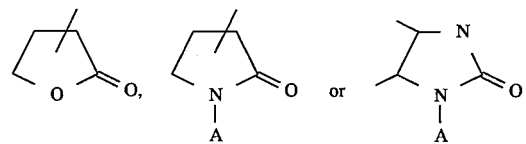

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —($CH_2$)$_n$COO$R^4$ where n=0–4 and $R^4$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, β-naphthyl; $R^3$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

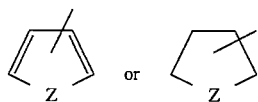

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

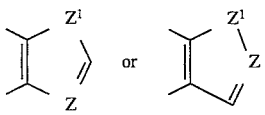

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

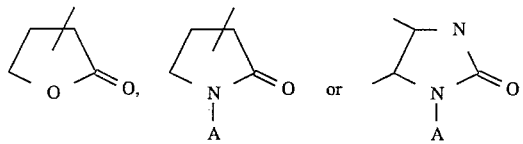

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —$(CH_2)_n COOR^4$ where n=0–4 and $R^4$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^2$ and $R^3$ cannot both be hydrogen;

or $R^2$ and $R^3$ taken together are —$(CH_2)_2B(CH_2)_2$—, wherein B is selected from $(CH_2)_n$ and n=0–1, —NH, —N($C_1$–$C_3$)alkyl [straight or branched], —N($C_1$–$C_4$)alkoxy, oxygen, sulfur or substituted congeners selected from (L or D)proline, ethyl (L or D) prolinate, morpholine, pyrrolidine or piperidine; and the pharmacologically acceptable organic and inorganic salts or metal complexes.

Particularly preferred compounds are compounds according to the above formula I and II wherein:

R is selected from hydrogen; straight or branched ($C_1$–$C_8$)alkyl group selected from methyl, ethyl, propyl, isopropyl, butyl, isobutyl, pentyl, hexyl, heptyl and octyl; α-mercapto($C_1$–$C_4$)alkyl group selected from mercaptomethyl, α-mercaptoethyl, α-mercapto-1-methylethyl and α-mercaptopropyl; α-hydroxy-($C_1$–$C_4$)alkyl group selected from hydroxymethyl, α-hydroxyethyl, α-hydroxy-1-methylethyl and α-hydroxypropyl; carboxyl($C_1$–$C_8$)alkyl group; ($C_6$–$C_{10}$)aryl group selected from phenyl, α-naphthyl and β-naphthyl; ($C_7$–$C_9$)aralkyl group selected from benzyl, 1-phenylethyl, 2-phenylethyl and phenylpropyl; $R^1$ is selected from hydrogen and ($C_1$–$C_6$)alkyl selected from methyl, ethyl, propyl, isopropyl, butyl, isobutyl, pentyl and hexyl;

when R does not equal $R^1$ the stereochemistry of the asymmetric carbon (i.e. the carbon bearing the W substituent) maybe be either the racemate (DL) or the individual enantiomers (L or D);

W is selected from amino; ($C_1$–$C_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl and decyl and the diastereomers and enantiomers of said branched alkyl monosubstituted amino group; ($C_3$–$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl and cyclooctyl and the diastereomers and enantiomers of said ($C_3$–$C_8$)cycloalkyl monosubstituted amino group; [($C_4$–$C_{10}$)cycloalkyl]alkyl monosubstituted amino group substitution selected from (cyclopropyl)methyl, (cyclopropyl)ethyl and (cyclobutyl)methyl; ($C_3$–$C_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl 2-cyclopentenyl and 2-cyclohexenyl; ($C_7$–$C_{10}$)aralkylamino group substitution selected from benzyl, 2-phenylethyl, 1-phenylethyl, 2-(naphthyl)methyl, 1-(naphthyl)methyl and phenylpropyl; straight or branched symmetrical disubstituted ($C_2$–$C_{14}$)alkylamino group substitution selected from dimethyl, diethyl, diisopropyl and di-n-propyl; straight or branched unsymmetrical disubstituted ($C_3$–$C_{14}$)alkylamino group wherein the total number of carbons in the substitution is not more than 14; unsymmetrical disubstituted ($C_4$–$C_{14}$)cycloalkylamino group wherein the total number of carbons in the substitution is not more than 14; ($C_2$–$C_8$)azacycloalkyl and substituted ($C_2$–$C_8$)azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, and trans-3,4-dimethylpyrrolidinyl and the diastereomers and enantiomers of said ($C_2$–$C_8$)azacycloalkyl and substituted ($C_2$–$C_8$)aza- cycloalkyl group; 1-azaoxacycloalkyl group selected from morpholinyl and 1-aza-5-oxacycloheptane; substituted 1-azaoxacycloalkyl group selected from 2-($C_1$–$C_3$)alkylmorpholinyl, 3-($C_1$–$C_3$)alkylisooxazolidinyl and tetrahydrooxazinyl; [1,n]-diazacycloalkyl and substituted [1,n]-diazacycloalkyl group selected from piperazinyl, 2-($C_1$–$C_3$)alkylpiperazinyl, 4-($C_1$–$C_3$)alkylpiperazinyl, 2,4-dimethylpiperazinyl, 4-hydroxypiperazinyl, 2,5-diazabicyclo[2.2.1]hept-2-yl, 2,5-diaza-5-methylbicyclo[ 2.2.1]hept-2-yl, and 2,3-diaza-3-methylbicyclo[ 2.2.2]oct-2-yl, the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl and 2-($C_1$–$C_3$)alkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl-1-pyrrolyl, 1-pyrazolyl, 3-($C_1$–$C_3$)alkyl-1-pyrazolyl, indolyl, 1-(1,2,3-triazolyl), 4-($C_1$–$C_3$)alkyl-1-(1,2,3-triazolyl), 5-($C_1$–$C_3$)alkyl- 1-(1,2,3-triazolyl) and 4-(1,2,4-triazolyl); (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group (substitution selected from straight or branched ($C_1$–$C_6$)alkyl); carboxy($C_2$–$C_4$)alkylamino group selected from aminoacetic acid, α-aminopropionic acid, β-aminopropionic acid, α-butyric acid, and β-aminobutyric acid and the enantiomers of said carboxy($C_2$–$C_4$)alkylamino group; ($C_1$–$C_4$)alkoxycarbonylamino group substitution selected from methoxycarbonyl, ethoxycarbonyl, allyloxycarbonyl, propoxycarbonyl, isoproxycarbonyl, 1,1-dimethylethoxycarbonyl, n-butoxycarbonyl, and 2-methylpropoxycarbonyl; ($C_1$–$C_4$)alkoxyamino group substitution selected from methoxy, ethoxy, n-propoxy, 1-methylethoxy, n-butoxy, 2-methylpropoxy, and 1,1-dimethylethoxy; ($C_7$–$C_{11}$)arylalkoxyamino group substitution selected from benzyoxy, 2-phenylethoxy, 1-phenylethoxy, 2-(naphthyl)methoxy, 1-(naphthyl)methoxy and phenylpropoxy;

$R^2$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

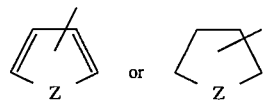

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

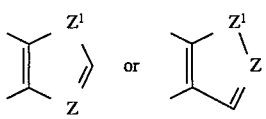

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

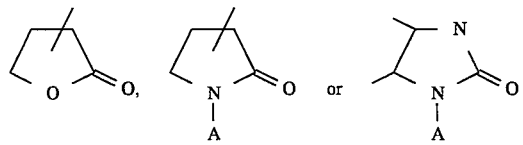

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$) alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl- 2-dioxo-1-piperazinyl, 2-dioxomorpholinyl, 2-dioxothiomorpholinyl; or —(CH$_2$)$_n$COOR$^4$ where n=0–4 and $R^4$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, β-naphthyl; $R^3$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or γ-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

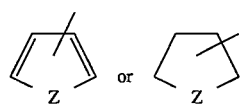

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

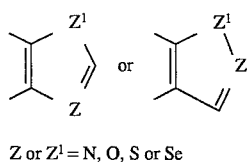

Z or Z¹ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

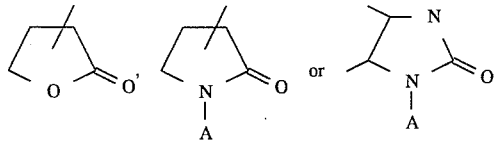

(A is selected from hydrogen; straight or branched $(C_1-C_4)$alkyl; $C_6$-aryl; substituted $C_6$-aryl (substitution selected from halo, $(C_1-C_4)$alkoxy, trihalo$(C_1-C_3)$alkyl, nitro, amino, cyano, $(C_1-C_4)$alkoxycarbonyl, $(C_1-C_3)$alkylamino or carboxy); $(C_7-C_9)$aralkyl group selected from benzyl, 1-phenylethyl, 2-phenylethyl or phenylpropyl)

such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or $(C_1-C_3)$alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxo-thiomorpholinyl; or $—(CH_2)_nCOOR^4$ where n=0–4 and $R^4$ is selected from hydrogen; straight or branched $(C_1-C_3)$alkyl selected from methyl, ethyl, n-propyl or 1-methylethyl; or $(C_6-C_{10})$aryl selected from phenyl, α-naphthyl or γ-naphthyl; with the proviso that $R^2$ and $R^3$ cannot both be hydrogen;

or $R^2$ and $R^3$ taken together are $—(CH_2)_2B(CH_2)_2—$, wherein B is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Compounds of special interest are compounds according to the above formula I and II wherein:

R is selected from hydrogen; straight or branched $(C_1-C_2)$alkyl group selected from methyl and ethyl;

$R^1$ selected from hydrogen or $(C_1-C_2)$alkyl selected from methyl and ethyl;

when R does not equal $R^1$ the stereochemistry of the asymmetric carbon (i.e. the carbon bearing the W substituent) maybe be either the racemate (DL) or the individual enantiomers (L or D);

W is selected from amino; $(C_1-C_8)$ straight or branched alkyl monosubstituted amino group substitution selected from methyl, ethyl, n-propyl, 1-methylethyl, n-butyl, 1-methylpropyl, 2-methylpropyl, n-hexyl and n-octyl; $(C_3-C_6)$cycloalkyl monosubstituted amino group substitution selected from cyclopropyl, cyclopentyl and cyclohexyl; [$(C_4-C_5)$cycloalkyl]alkyl monosubstituted amino group substitution selected from (cyclopropyl)methyl and (cyclopropyl)ethyl; $(C_3-C_4)$alkenyl monosubstituted amino group substitution selected from allyl and 3-butenyl; $(C_7-C_{10})$aralkylamino group substitution selected from benzyl, 2-phenylethyl and 1-phenylethyl; straight or branched symmetrical disubstituted $(C_2-C_4)$alkylamino group substitution selected from dimethyl and diethyl; straight or branched unsymmetrical disubstituted $(C_3)$alkylamino group substitution selected from methyl(ethyl); $(C_2-C_5)$azacycloalkyl group selected from pyrrolidinyl and piperidinyl; 1-azaoxacycloalkyl group selected from morpholinyl; substituted 1-azaoxacycloalkyl group selected from 2-$(C_1-C_3)$alkylmorpholinyl; [1,n]-diazacycloalkyl and substituted [1,n]-diazacycloalkyl group selected from piperazinyl, 2-$(C_1-C_3)$alkylpiperazinyl, 4-$(C_1-C_3)$alkylpiperazinyl, and 2,5-diaza-5-methylbicyclo [2.2.1]hept-2-yl and the diastereomers and enantiomers of said [1,n]-diazacycloalkyl and substituted [1,n]-diazacycloalkyl group; 1-azathiacycloalkyl and substituted 1-azathiacycloalkyl group selected from thiomorpholinyl and 2-$(C_1-C_3)$alkylthiomorpholinyl; N-azolyl group selected from 1-imidazolyl; (heterocycle)methylamino group selected from 2- or 3-thienylmethylamino and 2-, 3- or 4-pyridylmethylamino; $(C_1-C_4)$alkoxycarbonylamino group substitution selected from methoxycarbonyl, ethoxycarbonyl, and 1,1-dimethylethoxycarbonyl;

$R^2$ is selected from hydrogen; straight or branched $(C_1-C_3)$alkyl group selected from methyl, ethyl, n-propyl or 1-methylethyl;

$R^3$ is selected from hydrogen; straight or branched $(C_1-C_3)$alkyl group selected from methyl, ethyl, n-propyl or 1-methylethyl; with the proviso that $R^2$ and $R^3$ cannot both be hydrogen;

or $R^2$ and $R^3$ taken together are $—(CH_2)_2B(CH_2)_2—$, wherein B is selected from $(CH_2)_n$ and n=0–1, —NH, —N$(C_1-C_3)$alkyl [straight or branched], —N$(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Also included in the present invention are compounds useful as intermediates for producing the above compounds of formula I and II. Such intermediate include those having the formula III:

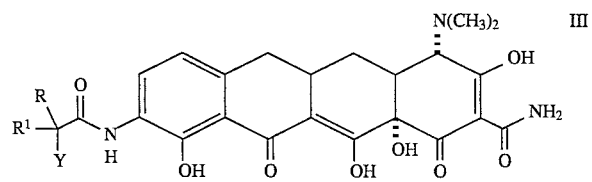

wherein:

Y is selected from $(CH_2)_nX$, n=0–5, X is halogen selected from bromine, chlorine, fluorine and iodine;

R is selected from hydrogen; straight or branched $(C_1-C_8)$alkyl group selected from methyl, ethyl, propyl, isopropyl, butyl, isobutyl, pentyl, hexyl, heptyl and octyl; α-mercapto$(C_1-C_4)$alkyl group selected from mercaptomethyl, α-mercaptoethyl, α-mercapto-1-methylethyl, α-mercaptopropyl and α-mercaptobutyl; α-hydroxy$(C_1-C_4)$alkyl group selected from hydroxymethyl, α-hydroxyethyl, α-hydroxy-1-methylethyl, α-hydroxypropyl and α-hydroxybutyl; carboxyl$(C_1-C_8)$alkyl group; $(C_6-C_{10})$aryl group selected from phenyl, α-naphthyl and β-naphthyl; substituted$(C_6-C_{10})$aryl group (substitution selected from hydroxy, halogen, $(C_1-C_4)$alkoxy, trihalo($C_1$–$C_3$)alkyl, nitro, amino, cyano, ($C_1$–$C_4$)alkoxycarbonyl, ($C_1$–$C_3$)alkylamino and carboxy); ($C_7$–$C_9$)aralkyl group selected from benzyl, 1-phenylethyl, 2-phenylethyl and phenylpropyl; substituted($C_7$–$C_9$)aralkyl group [substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy];

$R^1$ is selected from hydrogen and ($C_1$–$C_6$)alkyl selected from methyl, ethyl propyl, isopropyl, butyl, isobutyl, pentyl and hexyl;

when R does not equal $R^1$ the stereochemistry of the asymmetric carbon (i.e. the carbon bearing the W substituent) maybe be either the racemate (DL) or the individual enantiomers (L or D); and the pharmacologically acceptable organic and inorganic salts and metal complexes.

Preferred compounds are compounds according to the above formula III wherein:

Y is selected from $(CH_2)_nX$, n=0–5, X is halogen selected from bromine, chlorine, fluorine and iodine;

R is selected from hydrogen; straight or branched ($C_1$–$_8$)alkyl group selected from methyl, ethyl, propyl, isopropyl, butyl, isobutyl, pentyl, hexyl, heptyl and octyl; α-mercapto($C_1$–$C_4$)alkyl group selected from mercaptomethyl, α-mercaptoethyl, α-mercapto-1-methylethyl, α-mercaptopropyl and α-mercaptobutyl; α-hydroxy($C_1$–$C_4$)alkyl group selected from hydroxymethyl, α-hydroxyethyl, α-hydroxy-1-methylethyl, α-hydroxypropyl and α-hydroxybutyl; carboxyl($C_1$–$C_8$)alkyl group; ($C_6$–$C_{10}$)aryl group selected from phenyl, α-naphthyl and γ-naphthyl; ($C_7$–$C_9$)aralkyl group selected from benzyl, 1-phenylethyl, 2-phenylethyl and phenylpropyl; substituted($C_7$–$C_9$)aralkyl group [substitution selected from halo, ($C_1$–$C_4$)alkyl, nitro, hydroxy, amino, mono- or di-substituted ($C_1$–$C_4$)alkylamino, ($C_1$–$C_4$)alkoxy, ($C_1$–$C_4$)alkylsulfonyl, cyano and carboxy];

$R^1$ is selected from hydrogen and ($C_1$–$C_6$)alkyl selected from methyl, ethyl propyl, isopropyl, butyl, isobutyl, pentyl and hexyl;

when R does not equal $R^1$ the stereochemistry of the asymmetric carbon (i.e. the carbon bearing the W substituent) maybe be either the racemate (DL) or the individual enantiomers (L or D); and the pharmacologically acceptable organic and inorganic salts and metal complexes.

Particularly preferred compounds are compounds according to the above formula III wherein:

Y is selected from $(CH_2)_nX$, n=0–5, X is halogen selected from bromine, chlorine, fluorine and iodine;

R is selected from hydrogen; straight or branched ($C_1$–$C_8$)alkyl group selected from methyl, ethyl, propyl, isopropyl, butyl, isobutyl, pentyl, hexyl, heptyl and octyl; α-mercapto($C_1$–$C_4$)alkyl group selected from mercaptomethyl, α-mercaptoethyl, α-mercapto-1-methylethyl and α-mercaptopropyl; α-hydroxy($C_1$–$C_4$)alkyl group selected from hydroxymethyl, α-hydroxyethyl, α-hydroxy-1-methylethyl and α-hydroxypropyl; carboxyl($C_1$–$C_8$)alkyl group; ($C_6$–$C_{10}$)aryl group selected from phenyl, α-naphthyl and γ-naphthyl; ($C_7$–$C_9$)aralkyl group selected from benzyl, 1-phenylethyl, 2-phenylethyl and phenylpropyl; $R^1$ is selected from hydrogen and ($C_1$–$C_6$)alkyl selected from methyl, ethyl, propyl, isopropyl, butyl, isobutyl, pentyl and hexyl;

when R does not equal $R^1$ the stereochemistry of the asymmetric carbon (i.e. the carbon bearing the W substituent) maybe be either the racemate (DL) or the individual enantiomers (L or D); and the pharmacologically acceptable organic and inorganic salts and metal complexes.

Compounds of special interest are compounds according to the above formula III wherein:

Y is selected from $(CH_2)_nX$, n=0–5, X is halogen selected from bromine, chlorine, fluorine and iodine;

R is selected from hydrogen; straight or branched ($C_1$–$C_2$)alkyl group selected from methyl and ethyl; $R^1$ is selected from hydrogen and ($C_1$–$C_2$)alkyl selected from methyl and ethyl; when R does not equal $R^1$ the stereochemistry of the asymmetric carbon (i.e. the carbon bearing the W substituent) maybe be either the racemate (DL) or the individual enantiomers (L or D); and the pharmacologically acceptable organic and inorganic salts and metal complexes.

DESCRIPTION OF THE PREFERRED EMBODIMENTS.

The novel compounds of the present invention may be readily prepared in accordance with the following schemes.

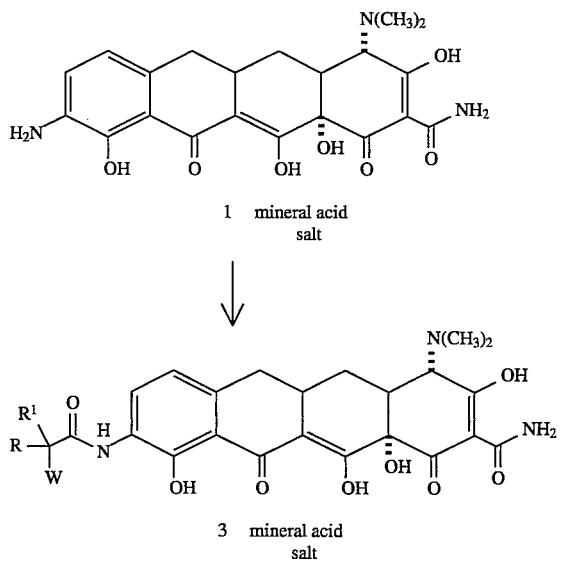

Scheme I

The 9-[(substituted glycyl)amido]-6-demethyl- 6-deoxytetracyclines, or mineral acid salts, can be made by the procedure described in scheme I. In accordance with scheme I, 9-amino-6-demethyl-6-deoxytetracycline or its mineral acid salt, 1, is dissolved in a mixture of 1,3-dimethyl-3,4, 5,6-tetrahydro-2(1H)-pyrimidone and acetonitrile. Sodium carbonate is added and the mixture is stirred for 5 minutes. An acid chloride of the formula:

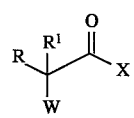

wherein R, $R^1$, W and X have been described hereinabove is added and the reaction is stirred at room temperature for from 0.5–2 hours to give the corresponding 9-[(substituted glycyl)amido]-6-demethyl- 6-deoxytetracycline, or its mineral acid salt 3.

Scheme II

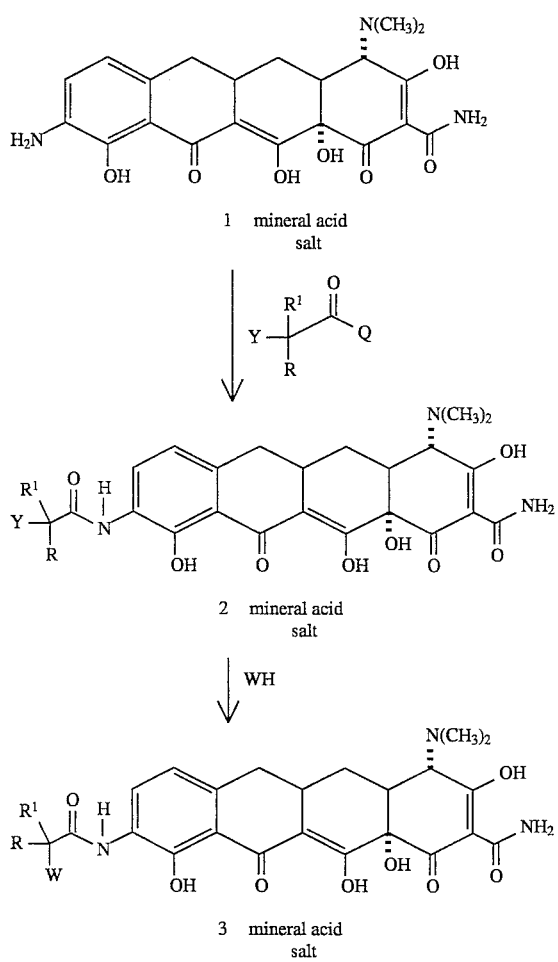

The preferred method for producing 9-[(substituted glycyl)amido]-6-demethyl-6-deoxytetracyclines or its mineral acid salt 3, is shown in scheme II. This method uses common intermediates which are easily prepared by reacting commercially available haloacyl halides of the formula:

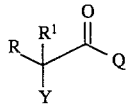

wherein Y, R and $R^1$ are as defined hereinabove and Q is halogen selected from bromine, chlorine, iodine and fluorine; with 9-amino-6-demethyl-6-deoxytetracyclines, or its mineral acid salt 1, to give straight or branched 9-[(haloacyl)amido]-6-demethyl-6-deoxytetracyclines or its mineral acid salt, 2, in almost quantitative yield. The above intermediates, straight or branched 9-[(haloacyl)amido]-6-demethyl-6-deoxytetracyclines or its mineral acid salt 2, react with a wide variety of nucleophiles, especially amines, having the formula WH, wherein W is as defined hereinabove to give the new 9-[(substituted glycyl)amido]-6-demethyl- 6-deoxytetracyclines or mineral acid salt 3 of the present invention.

In accordance with Scheme II, 9-amino-6-demethyl-6-deoxytetracycline or its mineral acid salt, 1, is mixed with a) a polar-aprotic solvent such as 1,3-dimethyl-3,4,5,6-tetrahydro-2(1H)pyrimidone, herein after called DMPU, hexamethylphosphoramide herein after called HMPA, dimethylformamide, dimethylacetamide, N-methylpyrrolidone, 1,2-dimethoxyethane or equivalent thereof;

b) an inert solvent such as acetonitrile, methylene chloride, tetrahydrofuran chloroform, carbon tetrachloride, 1,2-dichloroethane, tetrachloroethane, diethyl ether, t-butyl methylether, isopropyl ether or equivalent thereof;

c) a base such as sodium carbonate, sodium bicarbonate, sodium acetate, potassium carbonate, potassium bicarbonate, triethylamine, cesium carbonate, lithium carbonate or bicarbonate equivalents; and d) a straight or branched haloacyl halide of the formula:

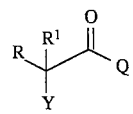

wherein Y, R, $R^1$ and Q are as defined hereinabove such as bromoacetyl bromide, chloroacetyl chloride or 2-bromopropionyl bromide or equivalent thereof; the halo, Y, and halide, Q, in the haloacyl halide can be the same or different halogen and is selected from bromine, chlorine, iodine and fluorine; Y is $(CH_2)_nX$, n=0–5, X is halogen;

e) for 0.5 to 5 hours at room temperature to the reflux temperature of the reaction; to form the corresponding 9-[(haloacyl)amido]-6-de-methyl-6-deoxytetracycline, 2, or its mineral acid salt.

The intermediate, 9-[(haloacyl)amido]-6-de-methyl-6-deoxytetracycline or mineral acid salt 2, is treated, under an inert atmosphere of helium, argon or nitrogen, with a) a nucleophile WH such as an amine or substituted amine or equivalent for example methylamine, dimethylamine, ethylamine, n-butylamine, propylamine or n-hexylamine;

b) a polar-aprotic solvent such as DMPU, HMPA dimethylformamide, dimethylacetamide, N-methylpyrrolidone or 1,2-dimethoxyethane;

c) for from 0.5–2 hours at room temperature or under reflux temperature to produce the desired 9-[(substituted glycyl)amido]-6-demethyl-6-deoxytetracycline, 3, or its mineral acid salt.

Scheme III

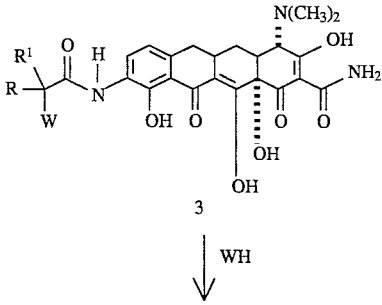

-continued
Scheme III

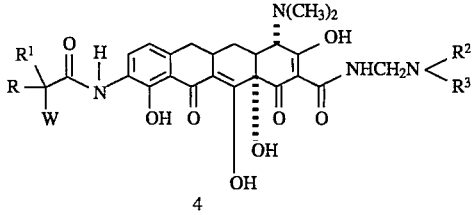

4

In accordance with Scheme III, compounds of formula 3 are N-alkylated in the presence of formaldehyde and either a primary amine such as methylamine, ethylamine, benzylamine, methyl glycinate, (L or D)alanine, (L or D)lysine or their substituted congeners; or a secondary amine such as morpholine, pyrrolidine, piperidine or their substituted congeners to give the corresponding Mannich base adduct, 4.

The 9-[(substituted glycyl)amido]-6-demethyl-6-deoxytetracyclines may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411–415, 1989). It is well known to one skilled in the art that an appropriate salt form is chosen based on physical and chemical stability, flowability, hygroscopicity and solubility. Preferably, the 9-[(substituted glycyl)amido]-6-demethyl-6-deoxytetracyclines are obtained as inorganic salt such as hydrochloric, hydrobromic, hydroiodic, phosphoric, nitric or sulfate; or organic salt such as acetate, benzoate, citrate, cysteine or other amino acids, fumarate, glycolate, maleate, succinate, tartrate, alkylsulfonate or arylsulfonate. Depending on the stochiometry of the acids used, the salt formation occurs with the C(4)-dimethylamino group (1 equivalent of acid) or with both the C(4)-dimethylamino group and the W group (2 equivalents of acid). The salts are preferred for oral and parenteral administration.

Some of the compounds of the hereinbefore described Schemes have centers of asymmetry at the carbon bearing the W substituent. The compounds may, therefore, exist in at least two (2) stereoisomeric forms. The present invention encompasses the racemic mixture of stereo isomers as well as all stereoisomers of the compounds whether free from other stereoisomers or admixed with stereoisomers in any proportion of enantiomers. The absolute configuration of any compound may be determined by conventional X-ray crystallography.

The stereochemistry centers on the tetracycline unit (i.e. C-4, C-4a, C-5a and C-12a) remain intact throughout the reaction sequences.

BIOLOGICAL ACTIVITY

Method for in Vitro Antibacterial Evaluation (Tables I, II and V)

The minimum inhibitory concentration (MIC), the lowest concentration of the antibiotic which inhibits growth to the test organism, is determined by the agar dilution method using Muller-Hinton II agar (Baltimore Biological Laboratories.). An inoculum density of $1–5\times10^5$ CFU/ml and a range of antibiotic concentrations (32–0.004 µg/ml) is used. The plates are incubated for 18 hours at 35° C. in a forced air incubator. The test organisms comprise strains that are sensitive to tetracycline and genetically defined strains that are resistant to tetracycline, due to inability to bind to bacterial ribosomes (tetM) or by a tetK encoded membrane protein which confers tetracycline resistance by energy-dependent efflux of the antibiotic from the cell.

E. coli in Vitro Protein Translation System (Table III)

An in vitro, cell free, protein translation system using extracts from E. coli strain MRE600 (tetracycline sensitive) and a derivative of MRE600 containing the tetM determinant has been developed based on literature methods [J. M. Pratt, Coupled Transcription-translation in Prokaryotic Cell-free Systems, Transcription and Translation, a Practical Approach, (B. D. Hames and S. J. Higgins, eds) p. 179–209, IRL Press, Oxford-Washington, 1984].

Using the system described above, the tetracycline compounds of the present invention are tested for their ability to inhibit protein sysnthesis in vitro. Briefly, each 10 µl reaction contains S30 extract (a whole extract) made from either tetracycline sensitive cells or an isogenic tetracycline resistant (tetM) strain, low molecular weight components necessary for transcription and translation (i.e. ATP and GTP), a mix of 19 amino acids (no methionine), $^{35}S$ labeled methionine, DNA template (either pBR322 or pUC119), and either DMSO (control) or the novel tetracycline compound to be tested ("novel TC") dissolved in DMSO.

The reactions are incubated for 30 minutes at 37° C. Timing is initiated with the addition of the S30 extract, the last component to be added. After 30 minutes, 2.5 µl of the reaction is removed and mixed with 0.5 ml of 1N NaOH to destroy RNA and tRNA. Two ml of 25% trichloroacetic acid is added and the mixture incubated at room temperature for 15 minutes. The trichloroacetic acid precipitated material is collected on Whatman GF/C filters and washed with a solution of 10% trichloroacetic acid. The filters are dried and the retained radioactivity, representing incorporation of $^{35}S$-methionine into polypeptides, is counted using standard liquid scintillation methods.

The percent inhibition (P.I.) of protein synthesis is determined to be:

$$P.I. = 100 - \left( \frac{\text{Retained radioactivity of novel TC containing sample}}{\text{Retained radioactivity of the DMSO control reaction}} \right) \times 100$$

In Vivo Antibacterial Evaluation (Table IV)

The therapeutic effects of tetracyclines are determined against an acute lethal infection with Staphylococcus aureus strain Smith (tetracycline sensitive). Female, mice, strain CD-1 (Charles River Laboratories), 20±2 grams, are challenged by an intraperitoneal injection of sufficient bacteria (suspended in hog mucin) to kill non-treated controls within 24–48 hours. Antibacterial agents, contained in 0.5 ml of 0.2% aqueous agar, are administered subcutaneously or orally 30 minutes after infection. When an oral dosing schedule is used, animals are deprived of food for-5 hours before and 2 hours after infection. Five mice are treated at each dose level. The 7 day survival ratios from 3 separate tests are pooled for calculation of median effective dose ($ED_{50}$).

Testing Results

The claimed compounds exhibit antibacterial activity against a spectrum of tetracycline sensitive and resistant Gram-positive and Gram-negative bacteria, especially, strains of *E. coli* and *S. aureus* containing tetM resistance determinants, and *E. coli* containing the tetA, tetB, tetC and tetD resistance determinants. Notable is 9-[(N,N-dimethylglycyl)amido]-6-demethyl-6-deoxytetracycline, CC, as shown in Table I, which demonstrated excellent in vitro activity against tetracycline resistant strains containing the tetM resistance determinant (such as *S. aureus* UBMS 88-5, *S. aureus* UBMS 90-1 and 90-2, *E. coli* UBMS 89-1 and 90-4) and tetracycline resistant strains containing tetB resistance determinants (such as *E. coli* UBMS 88-1 and *E. coli* TN10C tetB). 9-[(N,N-dimethylglycyl)amido]-6-demethyl-6-deoxytetracycline, also has good activity against *E. coli* strains containing tetA, tetC and tetD resistance determinants. It is as effective as minocycline against susceptible strains and is superior to minocycline against a number of recently isolated bacteria from clinical sources. (Table II)

As shown in Table II, the free base, disulfate, dihydrochloride, monohydrochloride and the Mannich bases of 9-[(N,N-dimethylglycyl)amindo]-6-de-methyl- 6-deoxytetracycline, show comparable in vitro antibacterial activity.

Minocycline and 9-[(N,N-dimethylglycyl)amido]-6-demethyl-6-deoxytetracycline are assayed for their ability to inhibit protein synthesis taking place on either wild type or TetM modified ribosomes using a coupled transcription and translation system. Both compounds effectively inhibit protein synthesis occurring on wild type ribosomes, at equivalent levels of activity. Minocycline is not effective in inhibiting protein synthesis occurring on tetM modified ribosomes. In contrast, 9-[(N,N-dimethylglycyl)amido]-6-demethyl-6-deoxytetracycline is effective at inhibiting protein synthesis occuring on TetM modified ribosomes, although a slightly higher concen-tration is required to achieve similar levels of inhibition relative to wild type ribosomes. (Table III)

9-[(N,N-Dimethylglycyl)amido]-6-demethyl-6-deoxytetracycline binds reversibly to its target (the ribosome) since bacterial growth resumes when the compound is removed by washing of the organism. Therefore, the ability of 9-[(N,N-dimethylglycyl)amido] -6-demethyl-6-deoxytetracycline to inhibit bacterial growth appears to be a direct consequence of its ability to inhibit protein synthesis at the ribosome level.

As shown in Table IV, the claimed compounds AA, BB, DD, CC, H, C, D, G and Q show very good in vivo activity when tested intraveneously against the minocycline sensitive organism, *S. aureus* Smith. The claimed compound CC when administered intraveneously exhibits potent activity ($ED_{50}$ 1.6 mg/kg) against *E. coli* UBMS 90-4 (TetM), which is resistant to minocycline, i.e. ($ED_{50}$>32 mg/kg).

As shown in Table V, 9-[(N,N-dimethylglycyl)amido)] -6-demethyl-6-deoxytetracycline shows potent in vitro antibacterial activity against a broad spectrum of recent clinical isolates, including a number from veterinary sources. It was more active than minocycline and tetracycline against the majority of the isolates tested. The claimed compound is especially active against *E. faecalis, E. faecium* including vancomycin resistant strains. The 9-[(dimethylglycyl)amido] -6-demethyl-6-deoxytetracycline also exhibits potent activity against *E. coli, Salmonella spp., Shigella spp., Salmonella choleraesuis, Proteus mirabilis, Proteus vulgaris, Morganella morganii, Neisseria gonorrhoeae, Bacteroides spp., Clastridium spp.* and *Streptococcus spp.* The activity of the 9-[(N,N-dimethylglycyl)amido]-6-demethyl-6-deoxytetracycline is generally greater than minocycline and tetracycline.

As can be seen from Tables I–V, compounds of the invention can be used to prevent or control important mammalian and veterinary diseases such as diarrhea, urinary tract infections, infections of skin and skin structure, ear, nose and throat infections, wound infections, mastitis and the like.

Thus, the improved efficacy of 9-[(N,N-dimethylglycyl)amido] -6-demethyl-6-deoxytetracycline is demonstrated by the in vitro activity against isogenic strains into which the resistance determinants, such as tetM, are cloned (Table I); the inhibition of protein synthesis by TetM modified ribosomes (Table III); and the in vivo activity against experimental infections caused by strains resistant to the tetracyclines, due to the presence of resistance determinants, such as tet M (Table IV).

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserve against the contaminating action of micoorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not be construed as limiting the scope of the invention.

| | COMPOUND LEGEND FOR TABLES |
|---|---|
| A | [7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-4-methyl-1-piperidineacetamide dihydrochloride |
| B | [4S-(4alpha,12aalpha)]-4-(Dimethylamino)-9-[[2-(dimethylamino)-1-oxopropyl]amino]-1,4,4a,5,5a,6,11,12a-octahydro-3,10,12,12a-tetrahydroxy-1,11-dioxo-2-naphthacenecarboxamide dihydrochloride |
| C | [4S-(4alpha,12aalpha)]-4-(Dimethylamino)-1,4,4a,5,5a,6,11,12a-octahydro-3,10,12,12a-tetrahydroxy-1,11-dioxo-9-[[(propylamino)acetyl]amino]-2-naphthacenecarboxamide dihydrochloride |
| D | [7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-1-pyrrolidineacetamide dihydrochloride |
| E | [4S-(4alpha,12aalpha)]-4-(Dimethylamino)-9-[[(ethylamino)acetyl]amino]-1,4,4a,5,5a,6,11,12a-octahydro-3,10,12,12a-tetrahydroxy-1,11-dioxo-2-naphthacenecarboxamide dihydrochloride |
| F | [4S-(4alpha,12aalpha)]-4-(Dimethylamino)-1,4,4a,5,5a,6,11,12a-octahydro-3,10,12,12a-tetrahydroxy-9-[[(methylamino)acetyl]amino]-1,11-dioxo-2-naphthacenecarboxamide dihydrochloride |
| G | [4S-(4alpha,12aalpha)]-4-(Dimethylamino)-9-[[(hexylamino)acetyl]amino]-1,4,4a,5,5a,6,11,12a-octahydro-3,10,12,12a-tetrahydroxy-1,11-dioxo-2-naphthacenecarboxamide dihydrochloride |
| H | [4S-(4alpha,12aalpha)]-9-[[(Butylamino)acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride |
| I | [7S-(7alpha,10aalpha)]-N-9-(Aminocarbonyl)-7-(dimethylamino)-5,5a,6,6a,7,10,10a,12-octahydro-1,8,10a,11-tetrahydroxy-10,12-dioxo-1-piperidineacetamide dihydrochloride (331,404) |
| J | [4S-(4alpha,12aalpha)]-4-(Dimethylamino)-1,4,4a,5,5a,6,11,12a-octahydro-3,10,12,12a-tetrahydroxy-1,11-dioxo-9-[[[(phenylmethyl)-amino]acetyl]amino]-2-naphthacenecarboxamide dihydrochloride |
| K | [4S-(4alpha,12aalpha)]-4-(Dimethylamino)-1,4,4a,5,5a,6,11,12a-octahydro-3,10,12,12a-tetrahydroxy-1,11-dioxo-9-[[(pentylamino)acetyl]amino]-2-naphthacenecarboxamide monohydrochloride |
| L | [4S-(4alpha,12aalpha)]-4-(Dimethylamino)-1,4,4a,5,5a,6,11,12a-octahydro-3,10,12,12a-tetrahydroxy-1,11-dioxo-9-[[[(2-thienylmethyl)-amino]acetyl)amino]-2-naphthacenecarboxamide dihydrochloride |
| M | [4S-(4alpha,12aalpha)]-4-(Dimethylamino)-1,4,4a,5,5a,6,11,12a-octahydro-3,10,12,12a-tetrahydroxy-9-[[[(2-methylpropyl)amino]acetyl]-amino]-1,11-dioxo-2-naphthacenecarboxamide dihydrochloride |
| N | [4S-(4alpha,12aalpha)]-4-(Dimethylamino)-1,4,4a,5,5a,6,11,12a-octahydro-3,10,12,12a-tetrahydroxy-1,11-dioxo-9-[[[(2-pyridinylmethyl]-amino]acetyl]amino]-2-naphthacenecarboxamide dihydrochloride |
| O | [4S-(4alpha,12aalpha)]-9-[[(Diethylamino)-acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride |
| P | [7S-(7alpha,10aalpha)]-N-9-(Aminocarbonyl)-7-(dimethylamino)-5,5a,6,6a,7,10,10a,12-octahydro-1,8,10a,11-tetrahydroxy-10,12-dioxo-2-naphthacenyl]-α-methyl-1-pyrrolidinecarboxamide |
| Q | [4S-(4alpha,12aalpha)]-9-[[[(Cyclopropyl-methyl)amino]acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride |
| R | [4S-(4alpha,12aalpha)]-9-[(Bromoacetyl)-amino]-4-(dimethylamino)-1,4,4a,5,5a,6,11,12a-octahydro-3,10,12,12a-tetrahydroxy-1,11-dioxo-2-naphthacenecarboxamide monohydrochlorid |
| S | [4S-(4alpha,12aalpha)]-9-[(2-Bromo-1-oxopropyl)amino]-4-(dimethylamino)-1,4,4a,5,5a,6,11,12a-octahydro-3,10,12,12a-tetrahydroxy-1,11-dioxo-2-naphthacenecarboxamide dihydrochloride |
| T | Tetracycline |
| U | Minocycline |
| AA | [4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide disulfate |
| BB | [4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide |
| CC | [4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide dihydrochloride |
| DD | [4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide monohydrochloride |
| EE | [4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-N-(1-pyrrolidinylmethyl)-2-naphthacenecarboxamide |

TABLE I

ANTIBACTERIAL ACTIVITY OF 9-[(SUBSTITUTED GLYCYL)AMIDO]-6-DEMETHYL-6-DEOXYTETRACYCLINES
MIC (μg/ml)

| Organism | Compound | | | | | | | | | | |
|---|---|---|---|---|---|---|---|---|---|---|---|
| | A | B | C | D | E | F | G | H | I | J | K |
| E. coli UBMS 88-1 Tet B | 1 | 1 | 0.5 | 0.25 | 0.5 | 1 | 1 | 0.25 | 1 | 4 | 1 |
| E. coli J3272 Tet sens | NT | NT | NT | NT | NT | NT | NT | 0.12 | NT | NT | NT |
| E. coli MC 4100 Tet sens. | 0.25 | 0.25 | 0.12 | 0.12 | 0.25 | 0.5 | 0.12 | NT | 0.25 | 0.5 | 0.5 |
| E. coli PRP1 Tet A | 1 | 2 | 1 | 0.25 | 2 | 4 | 1 | 0.25 | 1 | 4 | 0.5 |
| E. coli NC 4100 TNIOC Tet B | 1 | 0.5 | 0.5 | 0.25 | 1 | 1 | 1 | 0.25 | 1 | 4 | 0.5 |
| E. coli J3272 Tet C | 1 | 1 | 0.5 | 0.25 | 1 | 4 | 1 | 0.12 | 1 | 4 | 0.5 |
| E. coli UBMS 89-1 Tet M | 0.25 | 0.5 | 0.25 | 0.12 | 0.25 | 0.5 | 0.25 | 0.12 | 0.25 | 2 | 0.25 |
| E. coli UBMS 89-2 Tet sens. | 0.5 | 1 | 0.25 | 0.25 | 0.5 | 1 | 1 | 0.12 | 0.5 | 4 | 0.25 |
| E. coli J2175 | 0.5 | 1 | 0.25 | 0.25 | 0.5 | 0.5 | 1 | 0.25 | 0.5 | 4 | 0.5 |
| E. coli BAJ9003 IMP MUT | 0.12 | 0.25 | 0.06 | 0.06 | 0.12 | 0.5 | 0.12 | 0.06 | 0.12 | 0.5 | 0.25 |
| E. coli UBMS 90-4 Tet M | 0.5 | 0.5 | 0.25 | 0.25 | 0.25 | 0.5 | 0.5 | 0.12 | 0.5 | 4 | 0.5 |
| E. coli UBMS 90-5 | 0.5 | 0.5 | 0.25 | 0.25 | 0.5 | 0.5 | 1 | 0.12 | 0.5 | 4 | 0.5 |
| E. coli #311 (MP) | 0.25 | 0.5 | 0.5 | 0.25 | 0.5 | 0.5 | 1 | 0.12 | 0.5 | 4 | 0.5 |
| E. coli ATCC 25922 | 0.25 | 0.5 | 0.12 | 0.12 | 0.25 | 0.5 | 1 | 0.12 | 0.5 | 4 | 0.5 |
| E. coli J3272 Tet D | 0.25 | 0.5 | 0.12 | 0.12 | 0.25 | 0.5 | 0.5 | 0.06 | 0.5 | 4 | 0.5 |
| S. marcescens FPOR 8733 | 8 | 8 | 4 | 2 | 4 | 4 | 8 | 2 | 8 | >32 | 4 |
| X. maltophilia NEMC 87210 | 0.5 | 2 | 4 | 1 | 8 | 16 | 1 | 1 | 0.5 | 16 | 1 |
| Ps. aeruginosa ATCC 27853 | >32 | 32 | 16 | 16 | 16 | 32 | 32 | 8 | >32 | >32 | 32 |
| S. aureus NEMC 8769 | no growth | 0.06 | 0.06 | 0.06 | 0.12 | 0.25 | 0.12 | 0.03 | 0.5 | 1 | 0.12 |
| S. aureus UBMS 88-4 | 0.5 | 0.25 | 0.25 | 0.12 | 0.5 | 0.5 | 0.25 | 0.06 | 0.5 | 1 | 0.25 |
| S. aureus UBMS 88-5 Tet M | 0.5 | 0.5 | 0.5 | 0.12 | 0.5 | 1 | 0.5 | 0.06 | 0.5 | 2 | 0.5 |
| S. aureus USMS 88-7 Tet K | 1 | 1 | 2 | 0.5 | 8 | 16 | 1 | 1 | 0.5 | 4 | 2 |
| S. aureus UBMS 90-1 Tet M | 1 | 0.5 | 0.25 | 0.25 | 0.5 | 0.5 | 1 | 0.12 | 0.5 | 4 | 0.5 |
| S. aureus UBMS 90-3 | 0.5 | 0.06 | 0.06 | 0.12 | 0.12 | 0.5 | 0.25 | 0.03 | 0.25 | 0.5 | 0.25 |
| S. aureus UBMS 90-2 Tet M | 0.5 | 0.25 | 0.25 | 0.25 | 0.12 | 0.5 | 0.25 | 0.12 | 0.25 | 1 | 0.25 |
| S. aureus IVES 2943 | 0.5 | 1 | 4 | 1 | 16 | >32 | 2 | 1 | 1 | 4 | 2 |
| S. aureus ROSE (MP) | 2 | 4 | 16 | 2 | >32 | >32 | 4 | 4 | 4 | 8 | 8 |
| S. aureus SMITH (MP) | 0.5 | 0.25 | 0.12 | 0.12 | 0.25 | 0.5 | 0.25 | 0.12 | 0.25 | 0.5 | 0.25 |
| S. aureus IVES 1 983 | 1 | 1 | 4 | 1 | 8 | 16 | 1 | 2 | 1 | 4 | 2 |
| S. aureus ATCC 29213 | 0.5 | 0.25 | 0.25 | 0.12 | 0.5 | 0.5 | 0.5 | 0.06 | 0.5 | 1 | 0.5 |
| S. hemolyticus AVHAH 88-3 | 2 | 1 | 0.5 | 0.25 | 1 | 1 | 2 | 0.5 | 2 | 4 | 2 |
| Enterococcus 12201 | 0.5 | 0.25 | 0.25 | 0.12 | 0.25 | 0.5 | 0.25 | 0.12 | 0.25 | 2 | 0.25 |
| E. faecalis ATCC 29212 | 0.25 | 0.25 | 0.12 | 0.12 | 0.25 | 0.5 | 0.12 | 0.12 | 0.25 | 0.25 | 0.25 |

| Organism | Compound | | | | | | | | | |
|---|---|---|---|---|---|---|---|---|---|---|
| | L | M | N | O | P | Q | R | S | T | U |
| E. coli UBMS 88-1 Tet B | 32 | 1 | >32 | 1 | 2 | 0.5 | >32 | >32 | >32 | 16 |
| E. coli J3272 Tet sens | NT | NT | NT | NT | NT | NT | 32 | 4 | 1 | 1 |
| E. coli MC 4100 Tet sens. | 8 | 0.25 | 8 | 0.5 | 0.25 | 0.25 | NT | NT | 0.25 | 0.12 |
| E. coli PRP1 Tet A | 16 | 1 | 32 | 4 | 2 | 2 | >32 | >32 | 16 | 2 |
| E. coli NC 4100 TNIOC Tet B | 32 | 1 | 32 | 1 | 2 | 1 | >32 | >32 | >32 | 16 |
| E. coli J3272 Tet C | 32 | 1 | >32 | 1 | 1 | 0.5 | >32 | >32 | >32 | 1 |
| E. coli UBMS 89-1 Tet M | 8 | 0.5 | 16 | 0.5 | 0.5 | 0.5 | 8 | >32 | 32 | 8 |
| E. coli UBMS 89-2 Tet sens. | 16 | 1 | 32 | 1 | 1 | 1 | 32 | 16 | 1 | 1 |
| E. coli J2175 | 16 | 1 | >32 | 1 | 1 | 1 | 32 | 16 | 1 | 1 |
| E. coli BAJ9003 IMP MUT | 4 | 0.25 | 2 | 0.12 | 0.25 | 0.25 | 1 | 1 | 0.25 | 0.03 |
| E. coli UBMS 90-4 Tet M | 8 | 0.5 | 16 | 0.5 | 1 | 0.25 | 32 | >32 | 32 | >32 |
| E. coli UBMS 90-5 | 16 | 1 | 32 | 1 | 0.5 | 0.5 | 32 | 8 | 0.5 | 1 |
| E. coli #311 (MP) | 16 | 1 | 32 | 1 | 1 | 1 | 16 | 8 | 1 | 0.25 |
| E. coli ATCC 25922 | 8 | 0.5 | 32 | 0.5 | 1 | 0.5 | 16 | 8 | 0.5 | 0.25 |
| E. coli J3272 Tet D | 16 | 0.25 | 32 | 0.5 | 0.5 | 0.25 | >32 | >32 | >32 | 8 |
| S. marcescens FPOR 8733 | >32 | 8 | >32 | 8 | 16 | 8 | >32 | >32 | >32 | 4 |
| X. maltophilia NEMC 87210 | >32 | 2 | >32 | 1 | 4 | 4 | 16 | 16 | 8 | 0.12 |
| Ps. aeruginosa ATCC 27853 | >32 | 32 | >32 | 32 | >32 | 16 | >32 | >32 | 8 | 8 |
| S. aureus NEMC 8769 | 8 | 8 | 8 | 1 | 0.5 | 0.5 | 0.25 | 0.25 | 0.06 | ≦0.015 |
| S. aureus UBMS 88-4 | 8 | 0.5 | 8 | 0.5 | 0.5 | 0.5 | 0.5 | 2 | 0.12 | 0.03 |
| S. aureus UBMS 88-5 Tet M | 8 | 0.5 | 8 | 0.5 | 0.5 | 0.5 | 2 | 32 | =32 | 4 |
| S. aureus UBMS 88-7 Tet K | 16 | 2 | >32 | 0.5 | 1 | 8 | 8 | 16 | >32 | 0.06 |
| S. aureus UBMS 90-1 Tet M | 8 | 0.5 | 8 | 0.5 | 0.5 | 0.5 | 1 | 32 | >32 | 8 |
| S. aureus UBMS 90-3 | 4 | 0.25 | 4 | 0.25 | 0.25 | 0.5 | 1 | 2 | 0.12 | ≦0.015 |
| S. aureus UBMS 90-2 Tet M | 8 | 0.5 | 8 | 0.5 | 0.5 | 0.5 | 2 | 16 | 32 | 2 |
| S. aureus IVES 2943 | 16 | 4 | =32 | 1 | 2 | 8 | 16 | 32 | >32 | 2 |
| S. aureus ROSE (MP) | 32 | 8 | >32 | 2 | 8 | 16 | 16 | >32 | >32 | 0.25 |
| S. aureus SMITH (MP) | 4 | 0.5 | 4 | 0.25 | 0.5 | 0.5 | 1 | 1 | 0.12 | 0.03 |
| S. aureus IVES 1983 | 16 | 2 | >32 | 0.5 | 1 | 4 | 16 | 32 | >32 | 4 |
| S. aureus ATCC 29213 | 8 | 0.25 | 8 | 0.5 | 0.5 | 0.5 | 1 | 2 | ≦0.015 | ≦0.015 |
| S. hemolyticus AVHAH 88-3 | 8 | 2 | >32 | 2 | 4 | 4 | 8 | 8 | 0.5 | 0.06 |
| Enterococcus 12201 | 8 | 0.5 | 8 | 0.25 | 0.25 | 0.5 | 4 | 32 | 32 | 8 |
| E. faecalis ATCC 29212 | 4 | 0.25 | 4 | 0.25 | 0.25 | 0.25 | 2 | 16 | 16 | 2 |

TABLE II

ANTIBACTERIAL ACTIVITY OF 9-[(SUBSTITUTED GLYCYL)AMIDO]-6-DEMETHYL-6-DEOXYTETRACYCLINES MIC (μg/ml)

| Organism | AA | BB | CC | DD | EE | T | U |
|---|---|---|---|---|---|---|---|
| E. coli UBMS 88-1 Tet B | 0.25 | 0.25 | 0.25 | 0.25 | 0.5 | >32 | 16 |
| E. coli J3272 Tet sens | 0.25 | 0.12 | 0.12 | NT | NT | 1 | 1 |
| E. coli MC 4100 Tet sens. | NT | NT | NT | 0.06 | 0.12 | 0.25 | 0.12 |
| E. coli PRP1 Tet A | 2 | 0.5 | 0.5 | 1 | 2 | 16 | 2 |
| E. coli MC 4100 TNIOC Tet B | 0.25 | 0.25 | 0.25 | 0.25 | 0.5 | >32 | 16 |
| E. coli J3272 Tet C | 1 | 0.25 | 0.25 | 1 | 1 | 32 | 1 |
| E. coli UBMS 89-1 Tet M | 0.25 | 0.12 | 0.12 | 0.5 | 0.25 | 32 | 8 |
| E. coli UBMS 89-2 Tet sens. | 0.25 | 0.25 | 0.25 | 0.25 | 0.5 | 1 | 1 |
| E. coli J2175 | 0.25 | 0.25 | 0.25 | 0.25 | 0.5 | 1 | 1 |
| E. coli BAJ9003 IMP MUT | 0.06 | no growth | no growth | 0.06 | 0.12 | 0.25 | 0.03 |
| E. coli UBMS 90-4 Tet M | 0.25 | 0.12 | 0.12 | 0.12 | 0.25 | 32 | >32 |
| E. coli UBMS 90-5 | 0.25 | 0.12 | 0.12 | 0.25 | 0.25 | 0.5 | 1 |
| E. coli #311 (MP) | 0.50 | 0.12 | 0.12 | 0.25 | 0.5 | 1 | 0.25 |
| E. coli ATCC 25922 | 0.25 | 0.12 | 0.12 | 0.25 | 0.25 | 0.5 | 0.25 |
| E. coli J3272 Tet D | 0.12 | 0.06 | 0.03 | 0.25 | 0.25 | >32 | 8 |
| S. marcescens FPOR 8733 | 4 | 2 | 2 | 4 | 4 | >32 | 4 |
| X. maltophilia NEMC 87210 | 2 | 1 | 1 | 2 | 2 | 8 | 0.12 |
| Ps. aeruginosa ATCC 27853 | 16 | 8 | 4 | 8 | 16 | 8 | 8 |
| S. aureus NEMC 8769 | 0.03 | ≦0.015 | ≦0.015 | 0.03 | 0.25 | 0.06 | ≦0.015 |
| S. aureus UBMS 88-4 | 0.12 | 0.06 | 0.03 | 0.12 | 0.25 | 0.12 | 0.03 |
| S. aureus UBMS 88-5 Tet M | 0.12 | 0.12 | 0.03 | 0.12 | 0.25 | >32 | 4 |
| S. aureus UBMS 88-7 Tet K | 1 | 0.5 | 0.5 | 1 | 1 | >32 | 0.06 |
| S. aureus UBMS 90-1 Tet M | 0.25 | 0.12 | 0.06 | 0.12 | 0.25 | >32 | 8 |
| S. aureus UBMS 90-3 | 0.06 | 0.06 | 0.03 | 0.06 | 0.12 | 0.12 | ≦0.015 |
| S. aureus UBMS 90-2 Tet M | 0.12 | 0.12 | 0.06 | 0.12 | 0.25 | 32 | 2 |
| S. aureus IVES 2943 | 1 | 0.5 | 0.5 | 1 | 2 | >32 | 2 |
| S. aureus ROSE (MP) | 4 | 2 | 1 | 4 | 8 | >32 | 0.25 |
| S. aureus SMITH (MP) | 0.12 | 0.06 | 0.03 | 0.12 | 0.25 | 0.12 | 0.03 |
| S. aureus IVES 1983 | 2 | 0.5 | 0.5 | 1 | 2 | ≦32 | 4 |
| S. aureus ATCC 29213 | ≦0.015 | 0.3 | ≦0.015 | 0.12 | 0.25 | ≦0.015 | ≦0.015 |
| S. hemolyticus AVHAH 88-3 | 0.5 | 0.12 | 0.12 | 0.25 | 0.5 | 0.5 | 0.06 |
| Enterococcus 12201 | 0.12 | 0.06 | 0.03 | 0.12 | 0.25 | 32 | 8 |
| E. faecalis ATCC 29212 | 0.12 | 0.06 | 0.03 | 0.06 | 0.12 | 16 | 2 |

NT = not tested

TABLE III

In Vitro Transcription and Translation Sensitivity to 9-(Glycylamido)-6-deoxy-6-demethyltetracycline Derivatives

| Compound | Conc. | % Inhibition Wild Type S30 | % Inhibition Tet M S30 |
|---|---|---|---|
| CC | 1.0 mg/ml | 99 | 99 |
|  | 0.25 mg/ml | 98 | 94 |
|  | 0.06 mg/ml | 91 | 82 |
| H | 1.0 mg/ml | 99 | 98 |
|  | 0.25 mg/ml | 91 | 95 |
|  | 0.06 mg/ml | 86 | 72 |
| U | 1.0 mg/ml | 98 | 68 |
|  | 0.25 mg/ml | 89 | 43 |
|  | 0.06 mg/ml | 78 | 0 |

TABLE IV

Effects of Glycylcycline Derivatives on Acute Lethal Infections in Mice ($ED_{50}$ mg/kg)

| Organism | Route of Antibiotic Administration | AA | BB | DD | CC | H | C | D | G | Q | U |
|---|---|---|---|---|---|---|---|---|---|---|---|
| S. aureus Smith (Sens) | Oral | >16 | 8–16 | 12 | >8 | >16 | >16 | >16 | >16 | >16 | 0.74 |
|  | Intraveneous | 0.5–1 | 0.5–1 | 0.67 | 0.46 | 0.5–1 | 1–2 | 1–2 | >4 | NT | 0.37 |
| Escherichia coli UBMS 90-4 (Tet M) | Intraveneous | NT | NT | NT | 1.6 | NT | NT | NT | NT | NT | >32 |

TABLE V

In Vitro Activity of CC and Comparative Antibiotics vs Recent Clinical and Veterinary Isolates

| Organism | [# Isolates] | MIC (µg/ml) Range CC | U | T |
|---|---|---|---|---|
| *Staphylococcus aureus*, (methicillin-resistant) | [15] | 0.12–4 | 0.06–4 | 0.25–>64 |
| *Staphylococcus aureus*, (methicillin-susceptible) | [15] | 0.06–0.25 | 0.03–0.12 | 0.12–1 |
| *Staphylococcus* Coagulase-negative, (methicillin-resistant) | [16] | 0.06–16 | 0.03–1 | 0.12–>64 |
| *Staphylococcus* Coagulase-negative, (methicillin-susceptible) | [14] | 0.06–4 | 0.015–0.25 | 0.12–>64 |
| *Enterococcus faecalis* | [10] | 0.03–0.25 | 0.03–16 | 0.12–64 |
| *Enterococcus faecium* | [10] | 0.06–0.5 | 0.03–16 | 0.12–64 |
| Enterococcus spp. (Vancomycin-resistant) | [8] | 0.03–0.12 | 0.03–16 | 0.12–>64 |
| *Streptococcus pyogenes* | [10] | 0.06–0.12 | 0.03–2 | 0.12–16 |
| *Streptococcus agalactiae* | [10] | 0.12–0.25 | 0.12–16 | 0.25–64 |
| *Streptococcus pneumoniae* | [10] | 0.03–0.5 | 0.06–0.5 | 0.12–2 |
| *Listeria monocytogenes* | [8] | 0.06–0.12 | 0.015–0.03 | 0.12–0.5 |
| *Escherichia coli* | [30] | 0.25–4 | 0.25–32 | 0.5–>64 |
| *Escherichia coli* (Veterinary) | [15] | 0.25–4 | 1–16 | 2–>64 |
| Shigella spp. | [14] | 0.12–0.5 | 0.25–8 | 0.25–>64 |
| *Klebsiella pneumoniae* | [10] | 0.25–4 | 0.5–8 | 0.5–>64 |
| *Klebsiella oxytoca* | [10] | 0.25–1 | 0.5–4 | 0.5–1 |
| *Citrobacter freundii* | [10] | 0.5–8 | 0.03–32 | 0.5–16 |
| *Citrobacter diversus* | [10] | 0.25–1 | 0.25–4 | 0.5–4 |
| Salmonella spp. | [11] | 0.25–0.5 | 0.5–16 | 0.5–>64 |
| *Salmonella choleraesuis* (Veterinary) | [15] | 0.5–8 | 2–>64 | 1–>64 |
| *Serratia marcescens* | [10] | 2–8 | 1–8 | 8–>64 |
| *Enterobacter cloacae* | [10] | 0.5–1 | 0.25–4 | 0.5–2 |
| *Enterobacter aerogenes* | [10] | 0.25–1 | 0.5–1 | 0.5–1 |
| Providencia spp. | [13] | 1–8 | 4–>64 | 1–>64 |
| *Proteus mirabilis* | [26] | 0.12–2 | 1–32 | 0.5–64 |
| *Proteus vulgaris* | [18] | 0.06–1 | 0.5–16 | 0.25–64 |
| *Morganella morganii* | [16] | 0.5–1 | 0.25–32 | 0.25–>64 |
| *Pseudomonas aeruginosa* | [10] | 2–16 | 1–16 | 2–32 |
| *Xanthamonas maltophilia* | [10] | 1–8 | 0.12–1 | 8–16 |
| *Moraxella catarrhalis* | [18] | 0.06–0.12 | 0.03–0.12 | 0.06–0.5 |
| *Neisseria gonorrhoeae* | [14] | 0.5–1 | 0.5–64 | 1–>64 |
| *Haemophilus influenzae* | [15] | 1–2 | 0.5–2 | 1–32 |
| *Pasturella multocida* (Veterinary) | [17] | 0.03–0.25 | 0.015–4 | 0.06–16 |
| *Bordetella bronchiseptica* (Veterinary) | [10] | 0.06–0.12 | 0.06–0.12 | 0.12–0.25 |
| *Bacteroides fragiles* | [11] | 0.25–1 | <0.008–16 | 0.25–>64 |
| *Bacteroides fragiles* group | [10] | 0.12–2 | <0.008–4 | 0.25–32 |
| *Bacteroides* spp. | [9] | 0.12–0.5 | 0.03–16 | 0.25–>64 |
| *Clostridium difficile* | [12] | 0.06–0.12 | 0.015–16 | 0.12–32 |
| *Clostridium perfringens* | [16] | 0.03–2 | <0.008–16 | 0.015–16 |
| Clostridium spp. | [9] | 0.03–0.12 | <0.008–16 | 0.015–64 |
| Anaerobic Gram (+) Cocci | [15] | 0.015–0.12 | 0.05–8 | 4–>64 |

EXAMPLE 1

[4S-(4alpha,12aalpha)]-9-[(Bromoacetyl)amino]-4-(dimethylamino)-1,4,4a,5,5a,6,11,12a-octahydro-3,10,12,12 a-tetrahydroxy-1,11-dioxo-2-naphthacenecarboxamide Monohydrochloride and

[4S-(4alpha,12aalpha)]-9-[(Chloroacetyl)amino]-4-(dimethylamino)-1,4,4a,5,5a,6,11,12a-octahydro-3,10,12,12 a-tetrahydroxy-1,11-dioxo-2-naphthacenecarboxamide Monohydrochloride To a room temperature solution of 1.58 g of 9-amino-6-demethyl-6-deoxytetracycline monosulfate, 20 ml of 1,3-dimethyl-3,4,5,6-tetrahydro-2(1H)-pyrimidone, hereinafter called DMPU, and 4 ml of acetonitrile is added 0.50 g of sodium carbonate. The mixture is stirred for 5 minutes followed by the addition of 0.942 g of bromoacetyl chloride. The reaction is stirred for 1 hour, filtered, and the filtrate added dropwise to a mixture of 50 ml of isopropanol and 500 ml of diethyl ether. The resulting solid is collected, washed first with the mixed solvent (isopropanol and diethyl ether) followed by diethyl ether, and dried to give 1.62 g of a mixture of the desired products.

MS(FAB): m/z 550 (M+H) and 506 (M+H).

EXAMPLE 2

[4S-(4alpha,12aalpha)]-9-[(Bromoacetyl)amino]-4-(dimethylamino)-1,4,4a,5,5a,6,11,12a-octahydro-3,10,12,12 a-tetrahydroxy-1,11-dioxo-2-naphthacenecarboxamide Monohydrobromide The title compound is prepared by the procedure of Example 1 using 1.2 g of bromoacetyl bromide to give 1.49 g of the pure desired product.

$^1$H NMR(D$_6$-DMSO): δ 12.1(s,1H), 9.9(bs,1H), 9.8(s,1H), 9.55(s,1H), 9.05(s,1H), 8.05(d,1H), 6.8(d,1H), 4.3(s,1H), 4.2(s,2H), 2.75(s,6H).

EXAMPLE 3

[4S-(4alpha,12aalpha)]-9-[(Bromoacetyl)amino]-4-(dimethylamino)-1,4,4a,5,5a,6,11,12a-octahydro-3,10,12,12 a-tetrahydroxy-1,11-dioxo-2-naphthacenecarboxamide Monosulfate To a room temperature solution of 1.05 g of 9-amino-6-demethyl-6-deoxytetracycline monosulfate, 10 ml of DMPU and 2 ml of acetonitrile is added 0.605 g of bromoacetyl bromide. The mixture is stirred for 30 minutes, then poured slowly into a mixture of 5 ml methyl alcohol, 50 ml isopropyl alcohol and 500 ml of diethyl ether. The resulting yellow solid is collected, washed several times with diethyl ether and dried to give 1.27 g of the desired product.

$^1$H NMR(D$_6$-DMSO): δ 12.1(s,1H), 9.9(bs,1H), 9.8(s,1H), 9.55(s,1H), 9.05(s,1H), 8.05(d,1H), 6.8(d,1H), 4.3(s,1H), 4.2(s,2H), 2.75(s,6H).

EXAMPLE 4

[4S-(4alpha,12aalpha)]-9-[(Chloroacetyl)amino]-4-(dimethylamino)-1,4,4a,5,5a,6,11,12a-octahydro-3,10,12,12 a-tetrahydroxy-1,11-dioxo-2-naphthacenecarboxamide Monohydrochloride To a room temperature solution of 0.0465 g of 9-amino-6-demethyl-6-deoxytetracycline hydrochloride, 1.5 ml of DMPU and 0.5 ml of acetonitrile is added 0.023 g of chloroacetyl chloride. The mixture is stirred for 30 minutes, then poured into a mixture of 0.5 ml of methyl alcohol, 2 ml of isopropyl alcohol and 20 ml of diethyl ether. The resulting solid is collected, washed with diethyl ether and dried to give 0.042 g of the desired product.

MS(FAB): m/z 506 (M+H). $^1$H NMR(D$_6$-DMSO): δ 12.1(s,1H), 10.4(bs,1H), 9.75(s,1H), 9.55(s,1H), 9.05(s,1H), 8.05(d,1H), 6.8(d,1H), 4.4(s,2H), 4.3(s,1H), 2.8(s,6H).

EXAMPLE 5

[4S-(4alpha,12aalpha)]-9-[(2-Bromo-1-oxopropyl)-amino]-4-(dimethylamino)-1,4,4a,5,5a,6,11,12a-octahydro-3,10,12,12 a-tetrahydroxy-1,11-dioxo-2-naphthacenecarboxamide Monohydrobromide The title compound is prepared by the procedure of Example 1, using 2.11 g of 9-amino-4-(dimethylamino)-6-demethyl-6-deoxytetracycline monosulfate, 0.7 g of sodium carbonate, 20 ml of DMPU, ml of acetonitrile and 1.73 g of 2-bromopropionyl bromide. The reaction is stirred for 1 hour to give 1.75 g of the desired product. This reaction works equally well without sodium carbonate.

MS (FAB): m/z 564 (M+H).

EXAMPLE 6

[4S-(4alpha,12aalpha)]-4-(Dimethylamino)-9-[ [(hexyl-amino)acetyl]amino]-1,4,4a,5,5a,6,11,12a-octahydro-3,10,12,12a-tetrahydroxy-1,11-dioxo-2-naphthacenecarboxamide Dihydrochloride A mixture of 0.23 g of product from Example 2, 0.80 g of n-hexylamine and 5 ml of DMPU, under argon, is stirred at room temperature for 2 hours. The reaction is concentrated in vacuo and the residue diluted with a small volume of methanol. The diluted reaction solution is added dropwise to a mixture of 10 ml of isopropyl alcohol and 100 ml of diethyl ether. 2M hydrochloric acid in diethyl ether is added until a yellow solid is observed. The resulting solid is collected, washed with diethyl ether and dried to give 0.14 g of the desired product.

MS(FAB): m/z 571 (M+H).

Substantially following the methods described in detail herein above in Example 6, the compounds of this invention listed below in Examples 7–22 are prepared.

| Example # | Name | Starting Material Prod. of Exp. | Reactant | Rx Time | MS(FAB): m/z |
|---|---|---|---|---|---|
| 7 | [4S-(4alpha,12aalpha)]-4-(dimethyl-amino)-1,4,4a,5,5a,6,11,12a-octahydro-3,10,12,12a-tetrahydroxy-9-[[(methyl-amino)acetyl]amino]-1,11-dioxo-2-naphthacenecarboxamide dihydrochloride | 2 | Methylamine (40% in water) | 2.5 hrs. | 501(M + H) |
| 8 | [4S-(4alpha,12aalpha)]-4-(Dimethyl-amino)-9-[[(ethylamino)acetyl]amino]-1,4,4a,5,5a,6,11,12a-octahydro-3,10,-12,12a-tetrahydroxy-1,11-dioxo-2-naphthacenecarboxamide dihydrochloride | 2 | Ethylamine (70% in water) | 0.5 hr. | 515(M + H) |
| 9 | [7S-(7alpha,10aalpha)]-N-[9-(Amino-carbonyl)-7-(dimethylamino)-5,5a,6,6a,-7,10,10a,12-octahydro-1,8,10a,11-tetra-hydroxy-10,12-dioxo-2-naphthacenyl]-1-pyrrolidineacetamide dihydrochloride | 2 | Pyrrolidine | 0.5 hr. | 541(M + H) |
| 10 | [7S-(7alpha,10aalpha)]-N-[9-(Aminocar-bonyl)-7-(dimethylamino)-5,5a,6,6a,7,10,-10a,12-octahydro-1,8,10a,11-tetrahydroxy-10,12-dioxo-2-naphthacenyl]-4-methyl-1-piperidineacetamide dihydrochloride | 2 | 4-Methyl-piperidine | 1.5 hr. | 569(M 30 H) |
| 11 | [4S-(4alpha,12aalpha)]-4-(Dimethylamino)- | 2 | Propylamine | 1 hr. | 529(M + H) |

-continued

| Example # | Name | Starting Material Prod. of Exp. | Reactant | Rx Time | MS(FAB): m/z |
|---|---|---|---|---|---|
|  | 1,4,4a,5,5a,6,11,12a-octahydro-3,10,12,12a-tetrahydroxy-1,11-dioxo-9-[[(propylamino)-acetyl]amino]-2-naphthacenecarboxamide dihydrochloride |  |  |  |  |
| 12 | [4S-(4alpha,12aalpha)]-9-[[(Butyl-amino)acetyl]amino]-4-(dimethyl-amino)-1,4,4a,5,5a,6,11,12a-octa-hydro-3,10,12,12a-tetrahydroxy-1,11-dioxo-2-naphthacenecarboxamide dihydrochloride | 1 or 3 | n-Butylamine | 2 hr. | 543(M + H) |
| 13 | [4S-(4alpha,12aalpha)]-4-(Dimethyl-amino)-9-[[2-(dimethylamino)-1-oxo-propyl]amino]-1,4,4a,5,5a,6,11,12a-octahydro-3,10,12,12a-tetrahydroxy-1,11-dioxo-2-naphthacenecarboxamide dihydrochloride | 5 | Dimethylamine | 2 hr. | 529(M + H) |
| 14 | [4S-(4alpha,12aalpha)]-4-(Dimethyl-amino)-1,4,4a,5,5a,6,11,12a-octa-hydro-3,10,12,12a-tetrahydroxy-1,11-dioxo-9-[[(pentylamino)acetyl]amino]-2-naphthacenecarboxamide monohydro-chloride | 1 | Amylamine | 2 hr. | 557(M + H) |
| 15 | [7S-(7alpha,10aalpha)]-N-9-(Aminocar-bonyl)-7-(dimethylamino)-5,5a,6,6a,7,-10,10a,12-octahydro-1,8,10a,11-tetra-hydroxy-10,12-dioxo-1-piperidine-acetamide dihydrochloride | 3 | Piperidine | 1 hr. | 555(M + H) |
| 16 | [4S-(4alpha,12aalpha)]-4-(Dimethyl-amino)-1,4,4a,5,5a,6,11,12a-octa-hydro-3,10,12,12a-tetrahydroxy-1,11-dioxo-9-[[[(phenylmethyl)amino]-acetyl]amino]2-naphthacenecarbox-amide dihydrochloride | 3 | Benzylamine | 1 hr. | 577(M + H) |
| 17 | [4S-(4alpha,12aalpha)]-4-(Dimethyl-amino)-1,4,4a,5,5a,6,11,12a-octa-hydro-3,10,12,12a-tetrahydroxy-1,11-dioxo-9-[[[(2-thienylmethyl)amino]-acetyl]amino]-2-naphthacenecarboxamide dihydrochloride | 1 | 2-Thiophene-methylamine | 1½ hr. | 583(M + H) |
| 18 | [4S-(4alpha,12aalpha)]-4-(Dimethyl-amino)-1,4,4a,5,5a,6,11,12a-octa-hydro-3,10,12,12a-tetrahydroxy-9-[[[(2-methylpropyl)amino]acetyl]-amino]-1,11-dioxo-2-naphthacenecar-boxamide dihydrochloride | 3 | Isobutylamine | 1½ hr. | 543(M + H) |
| 19 | [4S-(4alpha,12aalpha)]-4-(Dimethyl-amino)-1,4,4a,5,5a,6,11,12a-octa-hydro-3,10,12,12a-tetrahydroxy-1,11-dioxo-9-[[[(2-pyridinylmethyl)amino]-acetyl]amino]-2-naphthacenecarboxamide dihydrochloride | 3 | 2-(Aminomethyl)pyridine | 1½ hr. | 578(M + H) |
| 20 | [4S-(4alpha,12aalpha)]-9-[[(Diethyl-amino)acetyl]amino]-4-(dimethylamino)-1,4,4a,5,5a,6,11,12a-octahydro-3,10,-12,12a-tetrahydroxy-1,11-dioxo-2-naphthacenecarboxamide dihydrochloride | 3 | Diethylamine | 1½ hr. | 543(M + H) |
| 21 | [7S-(7alpha,10aalpha)]-N-9-(Aminocar-bonyl)-7-(dimethylamino)-5,5a,6,6a,7,-10,10a,12-octahydro-1,8,10a,11-tetra-hydroxy-10,12-dioxo-2-naphthacenyl]-alpha-methyl-1-pyrrolidinecarboxamide | 5 | Pyrrolidine | 1 hr. | 555(M + H) |
| 22 | [4S-(4alpha,12aalpha)]-9-[[[(Cyclo-propylmethyl)amino]acetyl]amino]-4-(dimethylamino)-1,4,4a,5,5a,6,11,12a-tetrahydroxy-1,11-dioxo-2-naphthacene-carboxamide dihydrochloride | 3 | (Aminomethyl)cyclopropane | 1 hr. | 541(M + H) |

EXAMPLE 23

[4S-(4alpha,12aalpha)]-4-(Dimethylamino)-9-[ [(dimeth-ylamino)acetyl]amino]-1,4,4a,5, 5a,6,11,12a-octahydro-3,10,12,12a-tet-rahydroxy-1,11-dioxo-2-naphthacene-carboxamide Sulfate, Dihydrochloride, Monohydrochloride or Free Base A mixture of 0.264 g of 9-amino-6-demethyl-6-deoxytet-racycline, obtained by literature procedures, 5 ml of 1,3-dimethyl-3,4,5,6-tetrahydro-2(1H)pyrimidinone, 2 ml of acetonitrile and 0.3 g of sodium carbonate is stirred at room temperature for 5 minutes. To this mixture is added 0.094 g of N,N-dimethylglycyl chloride hydrochloride. The reaction is allowed to stir for 30 minutes at room temperature and then filtered. The filtrate is added dropwise to approximately 300 ml of diethyl ether containing a few drop of either concentrated sulfuric or hydrochloric acid. The resulting precipitate is collected, washed with diethyl ether and dried to yield 0.12 g of the desired product.

The hydrochloride salt is converted, by treatment with ammonium hydroxide, to the free base.

MS (FAB): m/z 515 (M+H).

Alternatively, the title compound is prepared by the procedure of Example 3, using 0.2 g of product from Example 1, 2, 3 or 4, 1.25 g of dimethylamine (40% in water) and 5 ml of DMPU to give 0.14 g of the desired product.

EXAMPLE 24

General Procedure for the Preparation of Mannich Bases

A mixture of 0.5 mm of product from Example 20 (free base), 3 ml of t-butyl alcohol, 0.55 mm of 37% formaldehyde, and 0.55 mm of pyrrolidine, morpholine or piperidine is stirred at room temperature for 30 minutes followed by heating at 100° C. for 15 minutes. The reaction mixture is cooled to room temperature and triturated with diethyl ether and hexane. The solid is collected, washed with diethyl ether and hexane, and dried to give the desired product. In this manner the following compound is made: [4S-(4alpha,12aalpha)]-4-(Dimethylamino)-9-[[(dimethylamino)acetyl] amino]-1,4,4a,5,5a,6,11,12a-octahydro-3,10,12,12 a-tetrahydroxy-1,11-dioxo-N-(1-pyrrolidinylmethyl)- 2-naphthacenecarboxamide Substantially following the method described in Example 6, the compounds of this invention listed below in Examples 25–48 are prepared using the product from Example 3 or 4.

EXAMPLE 25

[4S-(4alpha,12aalpha)]-4-(Dimethylamino)-1,4,4a,5,5a,6,11,12a-octahydro-3,10,12,12a-tetrahydroxy-9-[[(methoxyamino)acetyl]amino]-1,11-dioxo-2-naph-thacenecarboxamide

EXAMPLE 26

[4S-(4alpha,12aalpha)]-4-(Dimethylamino)-1,4,4a,5,5a,6,11,12a-octahydro-3,10,12,12a-tetrahydroxy- 1,11-dioxo-9-[[[(phenylmethoxy)amino]acetyl] amino]-2-naphthacenecarboxamide

EXAMPLE 27

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-4-ethyl-1H-pyrazole-1-acetamide

EXAMPLE 28

[4S-(4alpha,12aalpha)]-9-[[(Cyclobutylmethylamino)-acetyl]amino]-4-(dimethylamino)-1,4,4a,5,5a,6,11,12a-octahydro-3,10,12,12a-tetrahydroxy-1,11-dioxo-2-naphthacenecarboxamide

EXAMPLE 29

[4S-(4alpha,12aalpha)]-9-[[(2-Butenylamino)acetyl] amino]-4-(dimethylamino)-1,4,4a,5,5a,6,11,12a-octahydro-3,10,12,12a-tetrahydroxy-1,11-dioxo-2-naphthacenecarboxamide

EXAMPLE 30

[4S-(4alpha,12aalpha)]-4-(Dimethylamino)-1,4,4a,5,5a,6,11,12a-octahydro-3,10,12,12a-tetrahydroxy- 9-[[(hydroxyamino)acetyl]amino]-1,11-dioxo-2-naph-thacenecarboxamide

EXAMPLE 31

[4S-(4alpha,12aalpha)]-4-(Dimethylamino)-1,4,4a,5,5a,6,11,12a-octahydro-3,10,12,12a-tetrahydroxy-1,11-dioxo-9-[[[methyl(phenylmethyl)amino] acetyl]amino]-2-naphthacenecarboxamide

EXAMPLE 32

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-5-methyl-2,5-diazabicyclo[2.2.1]heptane-2-acetamide

EXAMPLE 33

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-3-methyl-4-morpholineacetamide

EXAMPLE 34

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-2-azabicyclo[2.2.1]heptane-2-acetamide

EXAMPLE 35

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-6-methyl-2-azabicyclo[2.2.2] octane-2-acetamide

EXAMPLE 36

[7S-(7alpha,10aalpha)]-N-[9-(Aminocarbonyl)-7-(dimethylamino)-5,5a,6,6a,7,10,10a,12-octahydro-1,8,10a,11-tetrahydroxy-1,12-dioxo-2-naphthacenyl]-4-methyl-1-piperazinecarboxamide

EXAMPLE 37

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-4-hydroxy-1-piperazineacetamide

EXAMPLE 38

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-3-methyl-1-piperazinecarboxamide

EXAMPLE 39

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-3-cyclopropyltetrahydro-4H-thiazine-4-acetamide

EXAMPLE 40

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-3-ethyl-1H-pyrrole-1-acetamide

EXAMPLE 41

[4S-(4alpha,12aalpha)]-4-(Dimethylamino)-1,4,4a,5,5a,6,11,12a-octahydro-3,10,12,12a-tetrahydroxy- 9-[[(1H-imidazol-2-ylmethylamino)acetyl] amino]-1,11-dioxo-2-naphthacenecarboxamide

EXAMPLE 42

[7S-(7alpha,10aalpha)]-N-[2-[[9-(Aminocarbonyl)-7-(dimethylamino)-5,5a,6,6a,7,10,10a,12-octahydro-1,8,10a,11-tetrahydroxy-10,12-dioxo-2-naphthacenyl] amino]-2-oxoethyl] alanine

EXAMPLE 43

[7S-(7alpha,10aalpha)]-N-[2-[[9-(Aminocarbonyl)-7-(dimethylamino)-5,5a,6,6a,7,10,10a,12-octahydro-1,8,10a,11-tetrahydroxy-10,12-dioxo-2-naphthacenyl-[-amino]-2-oxoethyl] carbamic acid 1,1-dimethylethyl ester

EXAMPLE 44

[4S-(4alpha,12aalpha)]-4-(Dimethylamino)-1,4,4a,5,5a,6,11,12a-octahydro-3,10,12,12a-tetrahydroxy-9-[[[[(2-methylcyclopropyl)oxy]amino]acetyl]amino]-1,11-dioxo-2-naphthacenecarboxamide

EXAMPLE 45

[4S-(4alpha,12aalpha)]-9-[[[(Bicyclo[2.2.2]oct-2-yloxy)amino]acetyl]amino]-4-(dimethylamino)-1,4,4a,5,5a,6,11,12a-octahydro-3,10,12,12a-tetrahydroxy-1,11-dioxo-2-naphthacenecarboxamide

EXAMPLE 46

[4S-(4alpha,12aalpha)]-4-(Dimethylamino)-1,4,4a,5,5a,6,11, 12a-octahydro-3,10,12,12a-tetrahydroxy- 9-[[[(3-methyl-2-butenyl)amino]acetyl]amino]-1,11-dioxo-2-naphthacenecarboxamide

EXAMPLE 47

[4S-(4alpha,12aalpha)]-4-(Dimethylamino)-1,4,4a,5,5a,6,11,12a-octahydro-3,10,12,12a-tetrahydroxy-9-[[[[4-[(2-methyl-1-oxopropyl)amino]phenyl]amino]acetyl]amino]-1,11-dioxo-2-naphthacenecarboxamide

EXAMPLE 48

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-3-ethyl-1-pyrrolidineacetamide Substantially following the method described in Example 6, the compounds of this invention listed below in Examples 49–55 are prepared using the product from Example 5.

EXAMPLE 49

[4S-(4alpha,12aalpha)]-4-(Dimethylamino)-1,4,4a,5,5a,6,11,12a-octahydro-3,10,12,12a-tetrahydroxy-9-[[2-[[(1-methyl-1H-imidazol-2-yl)methyl]amino]-1-oxopropyl]amino]-1,11-dioxo-2-naphthacenecarboxamide

EXAMPLE 50

[4S-(4alpha,12aalpha)]-9-[[2-(Dicyclopropylamino)-1-oxo-propyl]amino]-4-(dimethylamino)-1,4,4a,5,5a,6,11,12a-octahydro-3,10,12,12a-tetrahydroxy-1,11-dioxo-2-naphthacenecarboxamide

EXAMPLE 51

[7S-(7alpha,10aalpha)]-N-[9-(Aminocarbonyl)-7-(dimethyl-amino)-1,4,4a,5,5a,6,11,12a-octahydro-3,10,12,12a-tetra-hydroxy-10,12-dioxo-2-naphthacenyl]-4-methoxy-α-methyl-1-piperazinecarboxamide

EXAMPLE 52

[7S-(7alpha,10aalpha)]-N-[9-(Aminocarbonyl)-7-(dimethyl-amino)-5,5a,6,6a,7,10,10a,12-octahydro-1,8,10a,11-tetra-hydroxy-10,12-dioxo-2-naphthacenyl] tetrahydro-α,2-dimethyl-4H-1,4-thiazine-4-acetamide

EXAMPLE 53

[7S-(7alpha,10aalpha)]-[2-[[9-(Aminocarbonyl)-7-(dimethyl-amino)-5,5a,6,6a,7,10,10a,12-octahydro-1,8,10a,11-tetra-hydroxy-10,12-dioxo-2-naphthacenyl]amino]-2-oxo-1-methylethyl]carbamic acid 2-propenyl Ester

EXAMPLE 54

[7S-(7alpha,10aalpha)]-N-[9-(Aminocarbonyl)-7-(dimethyl-amino)-5,5a,6,6a,7,10,10a,12-octahydro-1,8,10a,11-tetra-hydroxy-10,12-dioxo-2-naphthacenyl]-4-(aminomethyl)-α-methyl-1-piperidineacetamide

EXAMPLE 55

[4S-(4alpha,12aalpha)]-4-(Dimethylamino)-1,4,4a,5,5a,6,11,12a-octahydro-3,10,12,12a-tetrahydroxy-9-[[2-[[3-(methyl-sulfonyl)phenyl]amino]-1-oxopropyl]amino]-1,11-dioxo-2-naphthacenecarboxamide Substantially following the method, described in detail herein above in Example 5, the compound of invention Example 56 is prepared.

EXAMPLE 56

[4S-(4alpha,12aalpha)]-9-[(2-Bromo-2-methyl-1-oxopropyl)amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 57

[4S-(4alpha,12aalpha)]-4-(Dimethylamino)-1,4,4a,5,5a,6,11,12a-octahydro-3,10,12,12a-tetrahydroxy-9-[[2-methyl-2-(methylamino)-1-oxopropyl]amino]-1,11-dioxo-2-naphthacenecarboxamide The titled compound is prepared by the procedure of Example 6. The reactants are the product from Example 56 and methylamine.

EXAMPLE 58

[4S-(4alpha,12aalpha)]-4-(Dimethylamino)-9-[[2-(dimethylamino)-2-methyl-1-oxopropyl]amino]-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 56 and dimethylamine.

Substantially following the method, described in detail herein above in Example 5, the compound of invention Example 59 is prepared.

EXAMPLE 59

[4S-(4alpha,12aalpha)]-9-[(2-Bromo-1-oxobutyl)amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 60

[4S-(4alpha,12aalpha)]-4-(Dimethylamino)-1,4,4a,5,5a,6,11,12a-octahydro-3,10,12,12a-tetrahydroxy-9-[[2-[[(3-methylcyclobutyl)oxy]amino]-1-oxobutyl]amino]-1,11-dioxo-2-naphthacenecarboxamide Hydrobromide The titled compound is prepared by the procedure of Example 6. The reactants are the product from Example 59 and methylcyclobutyloxyamine.

EXAMPLE 61

[4S-(4alpha,12aalpha)]-9-[[2-[(1,1-dimethylethyl)methylamino]-1-oxobutyl]amino]-4-(dimethylamino)-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 59 and N-methyl-t-butylamine.

EXAMPLE 62

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-α-ethyl-4-methyl-2-isoxazolidineacetamide The titled compound is prepared by the procedure of Example 6. The reactants are the product from Example 59 and 4-methyl-2-isoxazolidine.

EXAMPLE 63

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-α-ethyl-3-methyl-4H-1,2,4-triazole-4-acetamide The titled compound is prepared by the procedure of Example 6. The reactants are the product from Example 59 and 3-methyl-1,2,4-triazole.

Substantially following the method, described in detail herein above in Example 5, the compound of invention Example 64 is prepared.

EXAMPLE 64

[4S-(4alpha,12aalpha)]-9-[(2-Bromo-1-oxopentyl)amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 65

[4S-(4alpha,12aalpha)]-4-(Dimethylamino)-9-[[2-(dimethylamino)-3,3-dimethyl-1-oxobutyl]amino]-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 64 and dimethylamine.

Substantially following the method, described in detail herein above in Example 5, the compound of invention Example 66 is prepared.

EXAMPLE 66

[4S-(4alpha,12aalpha)]-9-[(2-Bromo-1-oxobutyl)amino]-4-(dimethylamino)-1,4,4a,5,5a,6,11,12a-octahydro-3,10,12,12a-tetrahydroxy-1,11-dioxo-2-naphthacenecar-boxamide Hydrobromide

EXAMPLE 67

[4S-(4alpha,12aalpha)]-4-(Dimethylamino)-9-[[2-(ethylamino)-2-methyl-1-oxobutyl]amino]-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 66 and ethylamine.

Substantially following the method, described in detail herein above in Example 5, the compound of invention Example 68 is prepared.

EXAMPLE 68

[4S-(4alpha,12aalpha)]-9-[(2-Bromo-3-hydroxy-1-oxopropyl)amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 69

[4S-(4alpha,12aalpha)]-4-(Dimethylamino)-9-[[2-(dimethylamino)-3-hydroxy-1-oxopropyl]amino]-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 68 and dimethylamine.

EXAMPLE 70

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10,12-dioxo-2-naphthacenyl]-α-(hydroxymethyl)-4-methyl-1H-imidazole-1-acetamide The titled compound is prepared by the procedure of Example 6. The reactants are the product from Example 68 and 4-methylimidazole.

Substantially following the method, described in detail herein above in Example 5, the compound of invention Example 71 is prepared.

EXAMPLE 71

[4S-(4alpha,12aalpha)]-9-[(2-Bromo-3-mercapto-1-oxopropyl)amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 72

[4S-(4alpha,12aalpha)]-9-[[2-(Diethylamino)-3-mercapto-1-oxopropyl]amino]-4-(dimethylamino)-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 71 and diethylamine.

EXAMPLE 73

[7S-(7alpha,10aalpha)]-N-[9-(Aminocarbonyl)-7-(dimethylamino)-5,5a,6,6a,7,10,10a,12-octahydro-1,8,10a,11-tetrahydroxy-10-12-dioxo-2-naphthacenyl]-α-(mercaptomethyl)-1-piperazineacetamide Substantially following the method, described in detail herein above in Example 5, the compound of invention Example 74 is prepared.

EXAMPLE 74

[7S-(7alpha,10aalpha)]-4-[[9-(Aminocarbonyl)-7-(dimethylamino)-5,5a,6,6a,7,10,10a,12-octahydro-1,8,10a,11-tetrahydroxy-10-12-dioxo-2-naphthacenyl] amino]-3-bromo-4-oxobutanoic Acid Hydrobromide

EXAMPLE 75

[7S-(7alpha,10aalpha]-4-[[9-(Aminocarbonyl)-7-(dimethylamino)-5,5a,6,6a,7,10,10a,12-octahydro-1,8,10a,11-tetrahydroxy-10,12-dioxo-2-dioxo-2-naphthacenyl] amino]-3-(hexylamino)-4-oxobutanoic Acid The titled compound is prepared by the procedure by Example 6. The reactants are the product from Example 74 and n-hexylamine.

EXAMPLE 76

[7S-(7alpha,10aalpha)]-4-[[9-(Aminocarbonyl)-7-(dimethylamino)-5,5a–6,6a,7,10,10a,12-octahydro-1,8,10a,11-tetrahydroxy-1,12-dioxo-2-naphthacenyl] amino]tetrahydro-6-(hydroxymethyl)-2H-1,2-isoxazine-2-propanoic Acid The titled compound is prepared by the procedure of Example 6. The reactants are the product from Example 74 and 6-(hydroxymethyl)-1,2-isoxazine.

EXAMPLE 77

[7S-(7alpha,10aalpha)]-4-[[9-(Aminocarbonyl)-7-(dimethylamino)-5,5a,6,6a,7,10,10a,12-octahydro-1,8,10a,11-tetrahydroxy-10,12-dioxo-2-naphthacenyl] amino]-3-[ethyl(phenylmethyl)amino]-4-oxobutanoic Acid The titled compound is prepared by the procedure of Example 6. The reactants are the product from Example 74 and N-ethylbenzylamine.

Substantially following the method, described in detail herein above in Example 5, the compound of invention Example 78 is prepared.

EXAMPLE 78

[7S-(7alpha,10aalpha)]-5-[[9-(Aminocarbonyl)-7-(dimethylamino)-5,5a,6,6a,7,10,10a,12-octahydro-1,8,10a-11-tetrahydroxy-10,12-dioxo-2-naphthacenyl] amino]-4-bromo-5-oxopentanoic Acid Hydrobromide

EXAMPLE 79

[7S-(7alpha,10aalpha)]-5-[[9-(Aminocarbonyl)-7-(dimethylamino)-5,5a,6,6a,7,10,10a,12-octahydro-1,8,10a,11-tetrahydroxy-10,12-dioxo-2-naphthacenyl] amino]-4-(cyclopropylamino)-5-oxopentanoic Acid The titled compound is prepared by procedure of Example 6. The reactants are the product from Example 78 and cyclopropylamine.

Substantially following the method, described in detail herein above in Example 5, the compound of invention Example 80 is prepared.

EXAMPLE 80

[4S-(4alpha,12aalpha)]-9-[(Bromophenylacetyl)amino]-4-(dimethylamino)-1,4,4a,5,5a,6,11,12a-octahydro-3,10,12,12a-tetrahydroxy-1,11-dioxo-2-naphthacene-carboxamide Hydrobromide

EXAMPLE 81

[4S-(4alpha,12aalpha)]-4-(Dimethylamino)-9-[[2-(dimethylamino)-2-phenylacetyl]amino]-1,4,4a,5,5a,6,11,12a-octahydro-3,10,12,12a-tetrahydroxy-1–11-dioxo-2-naphthacenecarboxamide The titled compound is prepared by the procedure of Example 6. The reactants are the product from Example 80 and dimethylamine.

Substantially following the method, described in detail herein above in Example 5, the compound of invention Example 82 is prepared.

EXAMPLE 82

[4S-(4alpha,12aalpha)]-9-[[Bromo(4-hydroxyphenyl)-acetyl]amino]-4-(dimethylamino)-1,4,4a,5,5a,6,11, 12a-octahydro-3,10,12,12a-tetrahydroxy-1,11-dioxo-2-naphthacenecarboxamide Hydrobromide

EXAMPLE 83

[4S-(4alpha,12aalpha)]-9-[[(Butylamino) (4-hydroxyphenyl)acetyl]amino]-4-(dimethylamino)-1,4,4a,5,5a,6,11,12a-octahydro-3,10,12,12a-tetra-hydroxy-1,11-dioxo-2-naphthacenecarboxamide The titled compound is prepared by the procedure of Example 6. The reactants are the product from Example 80 and dimethylamine.

Substantially following the method, described in detail herein above in Example 5, the compound of invention Example 84 is prepared.

EXAMPLE 84

[4S-(4alpha,12aalpha)]-9-[[Bromo(4-methoxyphenyl)-acetyl]amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 85

[4S-(4alpha,12aalpha)]-4-(Dimethylamino)-9-[2-(dimethylamino)-3-(4-methoxyphenyl)-1-oxopropyl]-1,4,4a,5,5a,6,11,12a-octahydro-3,10,12,12a-tetrahydroxy-1–11-dioxo-2-naphthacenecarboxamide The titled compound is prepared by the procedure of Example 6. The reactants are the product from Example 84 and dimethylamine.

Substantially following the method, described in detail herein above in Example 5, the compound of invention Example 86 is prepared.

EXAMPLE 86

[4S-(4alpha,12aalpha)]-9-[[Bromo[4-(trifluoromethyl)-phenyl]acetyl]amino]-4-(dimethylamino)-1,4,4a,5,5a,6,11,12a-octahydro-3,10,12,12a-tetrahydroxy-1,11-dioxo-2-naphthacenecarboxamide Hydrobromide

EXAMPLE 87

[4S-(4alpha,12aalpha)]-4-(Dimethylamino)-9-[[2-(ethylmethylamino)-3-[4-(trifluoromethyl)phenyl]-1-oxopropyl]amino]-1,4,4a,5,5a,6,11,12a-octahydro-3,10,12,12a-tetrahydroxy-1,11-dioxo-2-naphthacene-carboxamide The titled compound is prepared by the procedure ofxample 6. The reactants are the product from Example 86 and N-ethylmethylamine.

Substantially following the method, described in detail herein above in Example 5, the compound of invention Example 88 is prepared.

EXAMPLE 88

[4S-(4alpha,12aalpha)]-9-[[Bromo[4-(dimethylamino)-phenyl]acetyl]amino]-4-(dimethylamino)-1,4,4a,5,5a,6,11,12 a-octahydro-3,10,12,12a-tetrahydroxy-1,11-dioxo-2-naphthacenecarboxamide Hydrobromide

EXAMPLE 89

[4S-(4alpha,12aalpha)]-4-(Dimethylamino)-9-[[[4-(dimethylamino)phenyl](2-propenylamino)acetyl] amino]-1,4,4a,5,5a,6,11,12a-octahydro-3,10,12,12a-tetrahydroxy-1,11-dioxo-2-naphthacenecarboxamide The titled compound is prepared by the procedure of Example 6. The reactants are the product from Example 88 and N-allylamine.

We claim:

1. A compound of the formula:

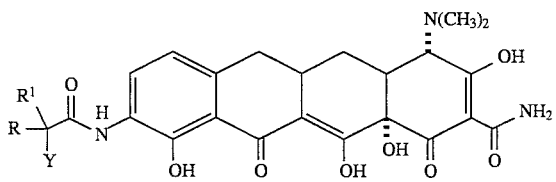

wherein:

Y is selected from $(CH_2)_n X$, n=0–5, X is halogen selected from bromine, chlorine, fluorine and iodine;

R is selected from hydrogen; straight or branched $(C_1-C_8)$alkyl group selected from methyl, ethyl, propyl, isopropyl, butyl, isobutyl, pentyl, hexyl, heptyl and octyl; α-mercapto$(C_1-C_4)$alkyl group selected from mercaptomethyl, α-mercaptoethyl, α-mercapto-1-methylethyl, α-mercaptopropyl and α-mercaptobutyl; α-hydroxy$(C_1-C_4)$alkyl group selected from hydroxymethyl, α-hydroxyethyl, α-hydroxy-1-methylethyl, α-hydroxypropyl and α-hydroxybutyl; carboxyl$(C_1-C_8)$alkyl group; $(C_6-C_{10})$aryl group selected from phenyl, α-naphthyl and β-naphthyl; substituted$(C_6-C_{10})$aryl group wherein the substitution is selected from hydroxy, halogen, $(C_1-C_4)$alkoxy, trihalo$(C_1-C_3)$ alkyl, nitro, amino, cyano, $(C_1-C_4)$alkoxycarbonyl, $(C_1-C_3)$alkylamino and carboxy; $(C_7-C_9)$aralkyl group selected from benzyl, 1-phenylethyl, 2-phenylethyl and phenylpropyl; substituted$(C_7-C_9)$aralkyl group wherein the substitution selected from halo, $(C_1-C_4)$alkyl, nitro, hydroxy, amino, mono- or di-substituted $(C_1-C_4)$alkylamino, $(C_1-C_4)$alkoxy, $(C_1-C_4)$alkylsulfonyl, cyano and carboxy;

$R^1$ is selected from hydrogen and $(C_1-C_6)$alkyl selected from methyl, ethyl, propyl, isopropyl, butyl, isobutyl, pentyl and hexyl;

when R does not equal $R^1$ the stereochemistry of the asymmetric carbon (i.e. the carbon bearing the Y substituent) maybe be either the racemate (DL) or the individual enantiomers (L or D); or a pharmacologically acceptable organic or inorganic salt or metal complex thereof.

2. The compound according to claim 1, wherein:

Y is selected from $(CH_2)_n X$, n=0–5, X is halogen selected from bromine, chlorine, fluorine and iodine;

R is selected from hydrogen; straight or branched $(C_1-C_8)$alkyl group selected from methyl, ethyl, propyl, isopropyl, butyl, isobutyl, pentyl, hexyl, heptyl and octyl; α-mercapto$(C_1-C_4)$alkyl group selected from mercaptomethyl, α-mercaptoethyl, α-mercapto-1-methylethyl, α-mercaptopropyl and α-mercaptobutyl; α-hydroxy$(C_1-C_4)$alkyl group selected from hydroxymethyl, α-hydroxyethyl, α-hydroxy-1-methylethyl and α-hydroxypropyl; carboxyl$(C_1-C_8)$alkyl group; $(C_6-C_{10})$aryl group selected from phenyl, α-naphthyl and β-naphthyl; $(C_7-C_9)$aralkyl group selected from benzyl, 1-phenylethyl, 2-phenylethyl and phenylpropyl; substituted$(C_7-C_9)$aralkyl group wherein the substitution is selected from halo, $(C_1-C_4)$alkyl, nitro, hydroxy, amino, mono- or di-substituted $(C_1-C_4)$alkylamino, $(C_1-C_4)$alkoxy, $(C_1-C_4)$ alkylsulfonyl, cyano and carboxy;

$R^1$ is selected from hydrogen and $(C_1-C_6)$alkyl selected from methyl, ethyl, propyl, isopropyl, butyl, isobutyl, pentyl and hexyl;

when R does not equal $R^1$ the stereochemistry of the asymmetric carbon (i.e. the carbon bearing the Y substituent) maybe be either the racemate (DL) or the individual enantiomers (L or D); or a pharmacologically acceptable organic or inorganic salt or metal complex thereof.

3. The compound according to claim 1, wherein:

Y is selected from $(CH_2)_n X$, n=0–5, X is halogen selected from bromine, chlorine, fluorine and iodine;

R is selected from hydrogen; straight or branched $(C_1-C_8)$alkyl group selected from methyl, ethyl, propyl, isopropyl, butyl, isobutyl, pentyl, hexyl, heptyl and octyl; α-mercapto$(C_1-C_4)$alkyl group selected from mercaptomethyl, α-mercaptoethyl, α-mercapto-1-methylethyl and α-mercaptopropyl; α-hydroxy$(C_1-C_4)$alkyl group selected from hydroxymethyl, α-hydroxyethyl, α-hydroxy-1-methylethyl and α-hydroxypropyl; carboxyl$(C_1-C_8)$alkyl group; $(C_6-C_{10})$aryl group selected from phenyl, α-naphthyl and β-naphthyl; $(C_7-C_9)$aralkyl group selected from benzyl, 1-phenylethyl, 2-phenylethyl and phenylpropyl; $R^1$ is selected from hydrogen and $(C_1-C_6)$alkyl selected from methyl, ethyl, propyl, isopropyl, butyl, isobutyl, pentyl and hexyl;

when R does not equal $R^1$ the stereochemistry of the asymmetric carbon (i.e. the carbon bearing the Y substituent) maybe be either the racemate (DL) or the individual enantiomers (L or D); or a pharmacologically acceptable organic or inorganic salt or metal complex thereof.

4. The compound according to claim 1, wherein:

Y is selected from $(CH_2)_n X$, n=0–5, X is halogen selected from bromine, chlorine, fluorine and iodine; R is selected from hydrogen; straight or branched $(C_1-C_2)$alkyl group selected from methyl and ethyl; $R^1$ is selected from hydrogen and $(C_1-C_2)$alkyl selected from methyl and ethyl;

when R does not equal $R^1$ the stereochemistry of the asymmetric carbon (i.e. the carbon bearing the Y substituent) maybe be either the racemate (DL) or the individual enantiomers (L or D); or a pharmacologically acceptable organic or inorganic salt or metal complex thereof.

5. The compound according to claim 1 wherein said inorganic salts comprise hydrochloric, hydrobromic, hydroiodic, phosphoric, nitric or sulfate.

6. The compound according to claim 1 wherein said organic salts comprise acetate, benzoate, citrate, cysteine or other amino acid, fumarate, glycolate, maleate, succinate, tartrate, alkylsulfonate or arylsulfonate.

7. The compound according to claim 1 wherein said metal complexes comprise aluminum, calcium, iron, magnesium, manganese or complex salts.

8. A compound according to claim 1, which is [4S-(4alpha,12aalpha)]-9-[(bromoacetyl)amino]-4-(dimethylamino)-1,4,4a,5,5a,6,11,12a-octahydro-3,10,12,12a-tetrahydroxy-1,11-dioxo-2-naphthacenecarboxamide monohydrochloride.

9. A compound according to claim 1, which is [4S-(4alpha,12aalpha)]-9-[(chloroacetyl)amino]-4-(dimethylamino)-1,4,4a,5,5a,6,11,12a-octahydro-3,10,12,12a-tetrahydroxy-1,11-dioxo-2-naphthacenecarboxamide monohydrochloride.

10. A compound according to claim 1, which is [4S-(4alpha,12aalpha)]-9-[(bromoacetyl)amino]-4-(dimethylamino)-1,4,4a,5,5a,6,11,12a-octahydro-3,10,12,12 a-tetrahydroxy-1,11-dioxo-2-naphthacenecarboxamide monohydrobromide.

11. A compound according to claim 1, which is [4S-(4alpha,12aalpha)]-9-[(bromoacetyl)amino]-4-(dimethylamino)-1,4,4a,5,5a,6,11,12a-octahydro-3,10,12.12a-tetrahydroxy-1,11-dioxo-2-naphthacenecarboxamide monosulfate.

12. A compound according to claim 1, which is [4S-(4alpha,12aalpha)]-9-[(2-bromo-1-oxopropyl)amino]-4-(dimethylamino)-1,4,4a,5,5a,6,11,12a-octahydro-3,10–12,12a-tetrahydroxy-1,11-dioxo-2-naphthacenecarboxamide monohydrobromide.

13. A compound according to claim 1, which is [4S-(4alpha,12aalpha)]-9-[(2-Bromo-2-methyl-1-oxopropyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

14. A compound according to claim 1, which is [4S-(4alpha,12aalpha)]-9-[(2-Bromo-1-oxobutyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

15. A compound according to claim 1, which is [4S-(4alpha,12aalpha)]-9-[(2-Bromo-1-oxopentyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

16. A compound according to claim 1, which is [4S-(4alpha,12aalpha)]-9-[(2-Bromo-1-oxobutyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

17. A compound according to claim 1, which is [4S-(4alpha,12aalpha)]-9-[(2-Bromo-3-hydroxy-1-oxopropyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

18. A compound according to claim 1, which is [4S-(4alpha,12aalpha)]-9-[(2-Bromo-3-mercapto-1-oxopropyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

19. A compound according to claim 1, which is [7S-(7alpha,10aalpha)]-4-[[9-(Aminocarbonyl)-7-(dimethylamino)-5,5a,6,6a,7,10,10a,12-octahydro-1,8,10a,11-tetrahydroxy-10–12-dioxo-2-naphthacenyl] amino]-3-bromo-4-oxobutanoic acid hydrobromide.

20. A compound according to claim 1, which is [7S-(7alpha,10aalpha)]-5-[[9-(Aminocarbonyl)-7-(dimethylamino)-5,5a,6,6a,7,10,10a,12-octahydro-1,8,10a-11-tetrahydroxy-10,12-dioxo-2-naphthacenyl] amino]-4-bromo-5-oxopentanoic acid hydrobromide.

21. A compound according to claim 1, which is [4S-(4alpha,12aalpha)]-9-[(Bromophenylacetyl)amino]-4-(dimethylamino)-1,4,4a,5,5a,6,11,12a-octahydro-3,10,12,12a-tetrahydroxy-1,11-dioxo-2-naphthacenecarboxamide hydrobromide.

22. A compound according to claim 1, which is [4S-(4alpha,12aalpha)]-9-[[Bromo(4-hydroxyphenyl)acetyl]amino]-4-(dimethylamino)-1,4,4a,5,5a,6,11,12a-octahydro-3,10,12,12a-tetrahydroxy-1,11-dioxo-2-naphthacenecarboxamide hydrobromide.

23. A compound according to claim 1, which is [4S-(4alpha,12aalpha)]-9-[[Bromo(4-methoxyphenyl)acetyl]amino]-4-(dimethylamino)-1,4,4a,5,5a,6,11,12a-octahydro-3,10,12,12a-tetrahydroxy-1,11-dioxo-2-naphthacenecarboxamide hydrobromide.

24. A compound according to claim 1, which is [4S-(4alpha,12aalpha)]-9-[[Bromo[4-(trifluoromethyl)phenyl]acetyl]amino]-4-(dimethylamino)-1,4,4a,5,5a,6,11,12a-octahydro-3,10,12,12a-tetrahydroxy-1,11-dioxo-2-naphthacenecarboxamide hydrobromide.

25. A compound according to claim 1, which is [4-S-(4alpha,12aalpha)]-9-[[Bromo[4-(dimethylamino)phenyl]acetyl]amino]-4-(dimethylamino)-1,4,4a,5,5a,6,11,12 a-octahydro-3,10,12,12a-tetrahydroxy-1,11-dioxo-2-naphthacenecarboxamide hydrobromide.

* * * * *